United States Patent
LaVon et al.

(10) Patent No.: US 10,869,786 B2
(45) Date of Patent: *Dec. 22, 2020

(54) ABSORBENT ARTICLES COMPRISING SENSORS

(71) Applicant: The Procter & Gamble Company, Cincinnati, OH (US)

(72) Inventors: Gary Dean LaVon, Liberty Township, OH (US); Vijay Rajagopalan, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/438,514

(22) Filed: Jun. 12, 2019

(65) Prior Publication Data

US 2019/0290502 A1 Sep. 26, 2019

Related U.S. Application Data

(63) Continuation of application No. 15/916,854, filed on Mar. 9, 2018, which is a continuation of application
(Continued)

(51) Int. Cl.
*A61F 13/42* (2006.01)
*A61F 13/505* (2006.01)
(Continued)

(52) U.S. Cl.
CPC ............ *A61F 13/505* (2013.01); *A61F 13/42* (2013.01); *A61F 13/496* (2013.01);
(Continued)

(58) Field of Classification Search
CPC ................ A61F 13/42; A61F 2013/422; A61F 2013/424; A61F 2013/425
See application file for complete search history.

(56) References Cited

U.S. PATENT DOCUMENTS

| 3,848,594 A | 11/1974 | Buell |
| 3,860,003 A | 1/1975 | Buell |

(Continued)

FOREIGN PATENT DOCUMENTS

| EP | 0149880 A2 | 7/1985 |
| EP | 1216673 A1 | 6/2002 |

(Continued)

OTHER PUBLICATIONS

16 C.F.R. Part 1501 and 1500.50-53, Jan. 2001.
(Continued)

*Primary Examiner* — Catharine L Anderson
(74) *Attorney, Agent, or Firm* — Brian M. Bolam; Andrew J. Hagerty

(57) ABSTRACT

A sensor system for detecting a property of or within an absorbent article may comprise an absorbent article and a sensor. The absorbent article may comprise a garment-facing layer and an absorbent assembly. The sensor may be disposed in and/or on the absorbent article. The sensor may be separable from the absorbent article. The sensor may be configured to sense a change in condition within the absorbent article.

20 Claims, 11 Drawing Sheets

Related U.S. Application Data

No. 13/483,456, filed on May 30, 2012, now Pat. No. 10,271,998.

(60) Provisional application No. 61/493,092, filed on Jun. 3, 2011, provisional application No. 61/493,095, filed on Jun. 3, 2011, provisional application No. 61/493,100, filed on Jun. 3, 2011.

(51) Int. Cl.

| | | |
|---|---|---|
| *A61F 13/496* | (2006.01) | |
| *A61F 13/58* | (2006.01) | |
| *A61F 13/62* | (2006.01) | |
| *A61F 13/84* | (2006.01) | |
| *A61F 13/80* | (2006.01) | |
| *A61F 13/514* | (2006.01) | |
| *G01N 27/04* | (2006.01) | |
| *G01N 33/487* | (2006.01) | |
| *H02J 7/00* | (2006.01) | |
| *A61F 13/15* | (2006.01) | |
| *G01N 21/84* | (2006.01) | |
| *G01N 27/02* | (2006.01) | |

(52) U.S. Cl.
CPC ...... *A61F 13/514* (2013.01); *A61F 13/51401* (2013.01); *A61F 13/51474* (2013.01); *A61F 13/58* (2013.01); *A61F 13/625* (2013.01); *A61F 13/80* (2013.01); *A61F 13/84* (2013.01); *G01N 27/048* (2013.01); *G01N 33/4875* (2013.01); *H02J 7/0027* (2013.01); *H02J 7/0045* (2013.01); *A61F 2013/1513* (2013.01); *A61F 2013/422* (2013.01); *A61F 2013/424* (2013.01); *A61F 2013/51441* (2013.01); *A61F 2013/8497* (2013.01); *G01N 21/84* (2013.01); *G01N 27/02* (2013.01)

(56) References Cited

U.S. PATENT DOCUMENTS

| | | | |
|---|---|---|---|
| 3,911,173 A | | 10/1975 | Sprague, Jr. |
| 4,022,210 A | | 5/1977 | Glassman |
| 4,265,245 A | | 5/1981 | Glassman |
| 4,286,331 A | | 8/1981 | Anderson et al. |
| 4,515,595 A | | 5/1985 | Kievit et al. |
| 4,554,662 A | | 11/1985 | Suzuki et al. |
| 4,573,986 A | | 3/1986 | Minetola et al. |
| 4,662,875 A | | 5/1987 | Hirotsu et al. |
| 4,681,793 A | | 7/1987 | Linman et al. |
| 4,695,278 A | | 9/1987 | Lawson |
| 4,699,622 A | | 10/1987 | Toussant et al. |
| 4,710,189 A | | 12/1987 | Lash |
| 4,785,996 A | | 11/1988 | Ziecker et al. |
| 4,795,454 A | | 1/1989 | Dragoo |
| 4,808,178 A | | 2/1989 | Aziz et al. |
| 4,842,666 A | | 6/1989 | Werenicz |
| 4,846,815 A | | 7/1989 | Scripps |
| 4,894,060 A | | 1/1990 | Nestegard |
| 4,908,803 A | | 3/1990 | Rialan |
| 4,909,803 A | | 3/1990 | Aziz et al. |
| 4,940,464 A | | 7/1990 | Van Gompel et al. |
| 4,946,527 A | | 8/1990 | Battrell |
| 4,963,140 A | | 10/1990 | Robertson et al. |
| 4,977,906 A | | 12/1990 | Di Scipio |
| 5,036,859 A | * | 8/1991 | Brown ................. A61F 5/48 |
| | | | 128/886 |
| 5,137,537 A | | 8/1992 | Herron et al. |
| 5,151,092 A | | 9/1992 | Buell et al. |
| 5,221,274 A | | 6/1993 | Buell et al. |
| 5,242,436 A | | 9/1993 | Weil et al. |
| 5,264,830 A | | 11/1993 | Kline et al. |
| 5,354,289 A | | 10/1994 | Mitchell et al. |
| 5,415,649 A | | 5/1995 | Watanabe et al. |
| 5,433,715 A | | 7/1995 | Tanzer et al. |
| 5,469,145 A | | 11/1995 | Johnson |
| 5,499,978 A | | 3/1996 | Buell et al. |
| 5,507,736 A | | 4/1996 | Clear et al. |
| 5,554,145 A | | 9/1996 | Roe et al. |
| 5,569,234 A | | 10/1996 | Buell et al. |
| 5,571,096 A | | 11/1996 | Dobrin et al. |
| 5,580,411 A | | 12/1996 | Nease et al. |
| 5,590,152 A | | 12/1996 | Nakajima et al. |
| 5,591,152 A | | 1/1997 | Buell et al. |
| 5,607,414 A | | 3/1997 | Richards et al. |
| 5,628,097 A | | 5/1997 | Benson et al. |
| 5,700,254 A | | 12/1997 | McDowall et al. |
| 5,709,222 A | | 1/1998 | Davallou |
| 5,714,156 A | | 2/1998 | Schmidt et al. |
| 5,760,694 A | | 6/1998 | Nissim |
| 5,817,087 A | | 10/1998 | Takabayashi et al. |
| 5,838,240 A | | 11/1998 | Johnson |
| 5,865,823 A | | 2/1999 | Curro |
| 5,902,222 A | | 5/1999 | Wessman |
| 5,938,648 A | | 8/1999 | LaVon et al. |
| 5,947,943 A | | 9/1999 | Lee |
| 5,959,535 A | | 9/1999 | Remsburg |
| 6,004,306 A | | 12/1999 | Robles et al. |
| 6,093,869 A | | 7/2000 | Roe et al. |
| 6,121,509 A | | 9/2000 | Ashraf et al. |
| 6,149,636 A | | 11/2000 | Roe et al. |
| 6,160,198 A | | 12/2000 | Roe et al. |
| 6,179,820 B1 | | 1/2001 | Fernfors |
| 6,203,496 B1 | | 3/2001 | Gael |
| 6,246,330 B1 | | 6/2001 | Nielsen |
| 6,264,643 B1 | | 7/2001 | Toyoda |
| 6,306,122 B1 | | 10/2001 | Narawa et al. |
| 6,372,951 B1 | | 4/2002 | Ter-Ovanesyan et al. |
| 6,384,296 B1 | | 5/2002 | Roe et al. |
| 6,432,098 B1 | | 8/2002 | Kline et al. |
| 6,501,002 B1 | | 12/2002 | Roe et al. |
| 6,534,149 B1 | | 3/2003 | Daley et al. |
| 6,583,722 B2 | | 6/2003 | Jeutter et al. |
| 6,603,403 B2 | | 8/2003 | Jeutter et al. |
| 6,609,068 B2 | | 8/2003 | Cranley et al. |
| 6,617,488 B1 | | 9/2003 | Springer et al. |
| 6,632,504 B1 | | 10/2003 | Gillespie et al. |
| 6,645,190 B1 | | 11/2003 | Olson et al. |
| 6,645,569 B2 | | 11/2003 | Cramer et al. |
| 6,761,711 B1 | | 7/2004 | Fletcher et al. |
| 6,817,994 B2 | | 11/2004 | Popp et al. |
| 6,840,928 B2 | | 1/2005 | Dana et al. |
| 6,849,067 B2 | | 2/2005 | Fletcher et al. |
| 6,863,933 B2 | | 3/2005 | Cramer et al. |
| 6,893,426 B1 | | 5/2005 | Popp et al. |
| 6,946,585 B2 | | 9/2005 | London Brown |
| 6,953,452 B2 | | 10/2005 | Popp et al. |
| 6,969,377 B2 | | 11/2005 | Koele et al. |
| 7,002,054 B2 | | 2/2006 | Allen et al. |
| 7,049,969 B2 | | 5/2006 | Tamai |
| 7,112,621 B2 | | 9/2006 | Rohrbaugh et al. |
| 7,145,053 B1 | | 12/2006 | Emenike et al. |
| 7,156,833 B2 | | 1/2007 | Courure-Dorschner et al. |
| 7,174,774 B2 | | 2/2007 | Pawar et al. |
| 7,201,744 B2 | | 4/2007 | Van Gompel et al. |
| 7,241,627 B2 | | 7/2007 | Wilhelm et al. |
| 7,250,547 B1 | | 7/2007 | Hofmeister et al. |
| 7,295,125 B2 | | 11/2007 | Gabriel |
| 7,355,090 B2 | | 4/2008 | Ales, III et al. |
| 7,394,391 B2 | | 7/2008 | Long |
| 7,410,479 B2 | | 8/2008 | Hoshino et al. |
| 7,449,614 B2 | | 11/2008 | Ales, III |
| 7,477,156 B2 | | 1/2009 | Long et al. |
| 7,489,252 B2 | | 2/2009 | Long et al. |
| 7,497,851 B2 | | 3/2009 | Koele et al. |
| 7,498,478 B2 | | 3/2009 | Long et al. |
| 7,504,550 B2 | | 3/2009 | Tippey et al. |
| 7,524,195 B2 | | 4/2009 | Ales et al. |
| 7,527,615 B2 | | 5/2009 | Roe et al. |
| 7,537,832 B2 | | 5/2009 | Carlucci et al. |
| 7,569,039 B2 | | 8/2009 | Matsuda et al. |
| 7,595,734 B2 | | 9/2009 | Long et al. |

(56) References Cited

U.S. PATENT DOCUMENTS

| | | |
|---|---|---|
| 7,642,396 B2 | 1/2010 | Ales, III et al. |
| 7,649,125 B2 | 1/2010 | Ales, III et al. |
| 7,659,815 B2 | 2/2010 | Cohen et al. |
| 7,667,806 B2 | 2/2010 | Kim et al. |
| 7,682,349 B2 | 3/2010 | Popp et al. |
| 7,700,820 B2 | 4/2010 | Tippey et al. |
| 7,700,821 B2 | 4/2010 | Ales, III et al. |
| 7,737,322 B2 | 6/2010 | Ales, III et al. |
| 7,744,579 B2 | 6/2010 | Langdon et al. |
| 7,753,691 B2 | 7/2010 | Ales et al. |
| 7,760,101 B2 | 7/2010 | Ales, III et al. |
| 7,786,341 B2 | 8/2010 | Schneider et al. |
| 7,789,869 B2 | 9/2010 | Berland et al. |
| 7,803,319 B2 | 9/2010 | Yang et al. |
| 7,812,731 B2 | 10/2010 | Bunza et al. |
| 7,834,235 B2 | 11/2010 | Long et al. |
| 7,835,925 B2 | 11/2010 | Roe et al. |
| 7,846,383 B2 | 12/2010 | Song |
| 7,850,470 B2 | 12/2010 | Ales et al. |
| 7,855,653 B2 | 12/2010 | Rondoni et al. |
| 7,862,550 B2 | 1/2011 | Koele et al. |
| 7,879,392 B2 | 2/2011 | Wenzel et al. |
| 7,946,869 B2 | 5/2011 | Ales et al. |
| 7,956,754 B2 | 6/2011 | Long |
| 7,973,210 B2 | 7/2011 | Long et al. |
| 7,977,529 B2 | 7/2011 | Bergman et al. |
| 8,007,485 B2 | 8/2011 | Popp et al. |
| 8,044,258 B2 | 10/2011 | Hietpas |
| 8,053,624 B2 | 11/2011 | Propp |
| 8,053,625 B2 | 11/2011 | Nhan et al. |
| 8,057,454 B2 | 11/2011 | Long et al. |
| 8,058,194 B2 | 11/2011 | Nhan et al. |
| 8,080,704 B2 | 12/2011 | Uchida, et al. |
| 8,101,813 B2 | 1/2012 | Ales et al. |
| 8,111,165 B2 | 2/2012 | Ortega et al. |
| 8,115,643 B2 | 2/2012 | Wada et al. |
| 8,134,042 B2 | 3/2012 | Song et al. |
| 8,172,982 B2 | 5/2012 | Ales et al. |
| 8,173,380 B2 | 5/2012 | Yang et al. |
| 8,183,876 B2 | 5/2012 | Wada et al. |
| 8,196,270 B2 | 6/2012 | Mandzsu et al. |
| 8,196,809 B2 | 6/2012 | Thorstensson |
| 8,207,394 B2 | 6/2012 | Feldkamp et al. |
| 8,215,973 B2 | 7/2012 | Ales et al. |
| 8,222,476 B2 | 7/2012 | Song et al. |
| 8,237,572 B2 | 8/2012 | Clement et al. |
| 8,248,249 B2 | 8/2012 | Clement et al. |
| 8,264,362 B2 | 9/2012 | Ales, III et al. |
| 8,274,393 B2 | 9/2012 | Ales et al. |
| 8,278,497 B2 | 10/2012 | Klofta |
| 8,299,317 B2 | 10/2012 | Tippey et al. |
| 8,304,598 B2 | 11/2012 | Mosbacher et al. |
| 8,314,284 B1 | 11/2012 | Novello |
| 8,334,226 B2 | 12/2012 | Nhan et al. |
| 8,334,425 B2 | 12/2012 | Ales et al. |
| 8,338,659 B2 | 12/2012 | Collins et al. |
| 8,350,694 B1 | 1/2013 | Trundle et al. |
| 8,361,048 B2 | 1/2013 | Kuen et al. |
| 8,372,052 B2 | 2/2013 | Popp et al. |
| 8,372,242 B2 | 2/2013 | Ales et al. |
| 8,372,766 B2 | 2/2013 | Nhan et al. |
| 8,378,167 B2 | 2/2013 | Allen et al. |
| 8,381,536 B2 | 2/2013 | Nhan et al. |
| 8,384,378 B2 | 2/2013 | Feldkamp et al. |
| 8,395,014 B2 | 3/2013 | Helmer et al. |
| 8,416,088 B2 | 4/2013 | Ortega et al. |
| 8,431,766 B1 | 4/2013 | Lonero |
| 8,440,877 B2 | 5/2013 | Collins et al. |
| 8,452,388 B2 | 5/2013 | Feldkamp et al. |
| 8,471,715 B2 | 6/2013 | Solazzo |
| 8,507,746 B2 | 8/2013 | Ong et al. |
| 8,518,009 B2 | 8/2013 | Saito et al. |
| 8,518,010 B2 | 8/2013 | Kuwano et al. |
| 8,546,639 B2 | 10/2013 | Wada et al. |
| 8,563,801 B2 | 10/2013 | Berland et al. |
| 8,570,175 B2 | 10/2013 | Rahimi |
| 8,579,876 B2 | 11/2013 | Popp et al. |
| 8,604,268 B2 | 12/2013 | Cohen et al. |
| 8,623,292 B2 | 1/2014 | Song et al. |
| 8,628,506 B2 | 1/2014 | Alex, III et al. |
| 8,642,832 B2 | 2/2014 | Ales et al. |
| 8,697,933 B2 | 4/2014 | Ales, III et al. |
| 8,697,934 B2 | 4/2014 | Nhan et al. |
| 8,697,935 B2 | 4/2014 | Daanen |
| 8,698,641 B2 | 4/2014 | Abraham et al. |
| 8,742,198 B2 | 6/2014 | Wei et al. |
| 8,747,379 B2 | 6/2014 | Fletcher et al. |
| D710,004 S | 7/2014 | Elkasas |
| 8,773,117 B2 | 7/2014 | Feldkamp et al. |
| 8,779,785 B2 | 7/2014 | Wada et al. |
| 8,785,716 B2 | 7/2014 | Schafer et al. |
| 8,816,149 B2 | 8/2014 | Richardson et al. |
| 8,866,052 B2 | 10/2014 | Nhan et al. |
| 8,866,624 B2 | 10/2014 | Ales, III et al. |
| 8,882,731 B2 | 11/2014 | Suzuki et al. |
| 8,884,769 B2 | 11/2014 | Novak |
| 8,889,944 B2 | 11/2014 | Abraham et al. |
| 8,920,731 B2 | 12/2014 | Nhan et al. |
| 8,933,291 B2 | 1/2015 | Wei et al. |
| 8,933,292 B2 | 1/2015 | Abraham et al. |
| 8,962,909 B2 | 2/2015 | Groosman et al. |
| 8,975,465 B2 | 3/2015 | Hong et al. |
| 8,978,452 B2 | 3/2015 | Johnson et al. |
| 8,988,231 B2 | 3/2015 | Chen |
| 9,018,434 B2 | 4/2015 | Ruman et al. |
| 9,018,435 B2 | 4/2015 | Kawashima |
| 9,034,593 B2 | 5/2015 | Martin et al. |
| 9,070,060 B2 | 6/2015 | Forster |
| 9,072,632 B2 | 7/2015 | LaVon et al. |
| 9,072,634 B2 | 7/2015 | Hundorf et al. |
| 9,168,185 B2 | 10/2015 | Berland et al. |
| 9,211,218 B2 | 12/2015 | Rinnert et al. |
| 9,295,593 B2 | 3/2016 | Van Malderen |
| 9,301,884 B2 | 4/2016 | Shah et al. |
| 9,314,381 B2 | 4/2016 | Curran et al. |
| 9,317,913 B2 | 4/2016 | Carney |
| 9,380,977 B2 | 7/2016 | Abir |
| 9,402,771 B2 | 8/2016 | Carney et al. |
| 9,421,137 B2 | 8/2016 | LaVon et al. |
| 9,545,342 B2 | 1/2017 | Cretu-Petra |
| 9,585,795 B2 | 3/2017 | Bosaeus et al. |
| 9,907,707 B2 * | 3/2018 | LaVon ................ H02J 7/0045 |
| 10,271,998 B2 | 4/2019 | Lavon |
| 2002/0021220 A1 | 2/2002 | Dreyer |
| 2002/0070864 A1 | 6/2002 | Jeutter et al. |
| 2003/0105190 A1 | 6/2003 | Diehl |
| 2003/0130637 A1 | 7/2003 | Intravartolo et al. |
| 2003/0148684 A1 | 8/2003 | Cramer et al. |
| 2003/0208133 A1 | 11/2003 | Mault |
| 2004/0036484 A1 * | 2/2004 | Tamai .................... A61F 13/42 |
| | | 324/663 |
| 2004/0064114 A1 | 4/2004 | David |
| 2004/0106202 A1 | 6/2004 | Zainiev et al. |
| 2004/0127867 A1 | 7/2004 | Odorzynski |
| 2004/0127878 A1 | 7/2004 | Olson et al. |
| 2004/0220538 A1 | 11/2004 | Panopoulos |
| 2004/0236302 A1 | 11/2004 | Wilhelm |
| 2004/0254549 A1 | 12/2004 | Olson et al. |
| 2005/0008839 A1 | 1/2005 | Cramer |
| 2005/0033250 A1 | 2/2005 | Collette et al. |
| 2005/0065487 A1 | 3/2005 | Graef |
| 2005/0099294 A1 | 5/2005 | Bogner |
| 2005/0107763 A1 | 5/2005 | Matsuda et al. |
| 2005/0124947 A1 | 6/2005 | Fernfors |
| 2005/0137542 A1 | 6/2005 | Underhill et al. |
| 2005/0156744 A1 | 7/2005 | Pires |
| 2005/0195085 A1 | 9/2005 | Cretu-Petra |
| 2006/0036222 A1 * | 2/2006 | Cohen .................... A61L 15/18 |
| | | 604/360 |
| 2006/0058745 A1 | 3/2006 | Pires |
| 2006/0061477 A1 | 3/2006 | Yeh |
| 2006/0069362 A1 | 3/2006 | Odorzynski et al. |
| 2006/0195068 A1 | 8/2006 | Lawando |
| 2006/0222675 A1 | 10/2006 | Sabnis |

(56) References Cited

U.S. PATENT DOCUMENTS

| | | |
|---|---|---|
| 2006/0224135 A1 | 10/2006 | LaVon et al. |
| 2006/0229578 A1 | 10/2006 | Roe et al. |
| 2006/0264861 A1 | 11/2006 | LaVon et al. |
| 2007/0044805 A1 | 3/2007 | Wedler et al. |
| 2007/0055210 A1 | 3/2007 | Kao |
| 2007/0142797 A1 | 6/2007 | Long et al. |
| 2007/0156106 A1 | 7/2007 | Klofta |
| 2007/0185467 A1 | 8/2007 | Klofta et al. |
| 2007/0233027 A1 | 10/2007 | Roe et al. |
| 2007/0252710 A1 | 11/2007 | Long et al. |
| 2007/0252711 A1 | 11/2007 | Long |
| 2007/0252713 A1 | 11/2007 | Rondoni et al. |
| 2007/0255241 A1 | 11/2007 | Weber et al. |
| 2007/0255242 A1 | 11/2007 | Ales, III et al. |
| 2007/0270774 A1 | 11/2007 | Bergman et al. |
| 2007/0282286 A1 | 12/2007 | Collins et al. |
| 2007/0287975 A1 | 12/2007 | Fujimoto et al. |
| 2008/0021423 A1 | 1/2008 | Klofta et al. |
| 2008/0021428 A1 | 1/2008 | Klofta |
| 2008/0052030 A1 | 2/2008 | Olson et al. |
| 2008/0054408 A1 | 3/2008 | Tippey et al. |
| 2008/0057693 A1 | 3/2008 | Tippey et al. |
| 2008/0058740 A1 | 3/2008 | Sullivan, Sr. |
| 2008/0058741 A1 | 3/2008 | Long |
| 2008/0058742 A1 | 3/2008 | Ales |
| 2008/0074274 A1 | 3/2008 | Hu et al. |
| 2008/0082062 A1 | 4/2008 | Cohen et al. |
| 2008/0082063 A1 | 4/2008 | Ales |
| 2008/0132859 A1 | 6/2008 | Pires |
| 2008/0147031 A1 | 6/2008 | Long |
| 2008/0208155 A1 | 8/2008 | LaVon et al. |
| 2008/0218334 A1 | 9/2008 | Pitchers et al. |
| 2008/0234644 A1 | 9/2008 | Hansson et al. |
| 2008/0266117 A1 | 10/2008 | Song |
| 2008/0266122 A1 | 10/2008 | Ales et al. |
| 2008/0266123 A1 | 10/2008 | Ales |
| 2008/0269707 A1 | 10/2008 | Song |
| 2008/0300559 A1 | 12/2008 | Gustafson et al. |
| 2008/0312622 A1 | 12/2008 | Hundorf |
| 2009/0058072 A1 | 3/2009 | Weber |
| 2009/0062756 A1 | 3/2009 | Long |
| 2009/0124990 A1 | 5/2009 | Feldkamp |
| 2009/0155753 A1 | 6/2009 | Ales et al. |
| 2009/0198202 A1 | 8/2009 | Nedestam |
| 2009/0275908 A1 | 11/2009 | Song |
| 2009/0326409 A1 | 12/2009 | Cohen |
| 2009/0326504 A1 | 12/2009 | Kaneda |
| 2010/0013778 A1 | 1/2010 | Liu et al. |
| 2010/0030173 A1 | 2/2010 | Song et al. |
| 2010/0125949 A1 | 5/2010 | Stebbing |
| 2010/0145294 A1 | 6/2010 | Song |
| 2010/0152688 A1 | 6/2010 | Handwerker |
| 2010/0159599 A1 | 6/2010 | Song |
| 2010/0159611 A1 | 6/2010 | Song |
| 2010/0160882 A1 | 6/2010 | Lowe |
| 2010/0164733 A1 | 7/2010 | Ales et al. |
| 2010/0168694 A1 | 7/2010 | Gakhar |
| 2010/0168695 A1 | 7/2010 | Robles |
| 2010/0168699 A1 | 7/2010 | Robles |
| 2010/0168700 A1 | 7/2010 | Schmidt |
| 2010/0168701 A1 | 7/2010 | Schmidt |
| 2010/0168702 A1 | 7/2010 | Ales, III |
| 2010/0241094 A1 | 9/2010 | Sherron |
| 2010/0277324 A1 | 11/2010 | Yeh |
| 2011/0004175 A1 | 1/2011 | Veith |
| 2011/0251038 A1 | 10/2011 | LaVon et al. |
| 2011/0298597 A1 | 12/2011 | Kaihori et al. |
| 2012/0061016 A1 | 3/2012 | Lavon et al. |
| 2012/0109087 A1 | 5/2012 | Abraham et al. |
| 2012/0116337 A1 | 5/2012 | Ales et al. |
| 2012/0116343 A1 | 5/2012 | Yoshioka et al. |
| 2012/0130330 A1 | 5/2012 | Wilson |
| 2012/0157947 A1* | 6/2012 | Nhan ............... A61F 13/42 |
| | | 604/361 |
| 2012/0161960 A1 | 6/2012 | Cheng |
| 2012/0172824 A1 | 7/2012 | Khaknazarov |
| 2012/0190956 A1 | 7/2012 | Connolly |
| 2012/0206265 A1 | 8/2012 | Solazzo |
| 2012/0225200 A1 | 9/2012 | Mandzsu et al. |
| 2012/0245541 A1 | 9/2012 | Suzuki et al. |
| 2012/0245542 A1 | 9/2012 | Suzuki |
| 2012/0256750 A1 | 10/2012 | Novak |
| 2012/0282681 A1 | 11/2012 | Teixeira |
| 2012/0299721 A1 | 11/2012 | Jones |
| 2012/0310190 A1 | 12/2012 | Lavon |
| 2012/0310191 A1 | 12/2012 | Lavon |
| 2012/0310192 A1 | 12/2012 | Suzuki |
| 2012/0323194 A1 | 12/2012 | Suzuki |
| 2013/0012896 A1 | 1/2013 | Suzuki |
| 2013/0018340 A1 | 1/2013 | Abraham |
| 2013/0023786 A1 | 1/2013 | Mani |
| 2013/0041334 A1 | 2/2013 | Prioleau |
| 2013/0076509 A1 | 3/2013 | Ahn |
| 2013/0110061 A1 | 5/2013 | Abraham |
| 2013/0110063 A1 | 5/2013 | Abraham |
| 2013/0110075 A1 | 5/2013 | Mukal et al. |
| 2013/0131618 A1 | 5/2013 | Abraham |
| 2013/0151186 A1 | 6/2013 | Feldkamp |
| 2013/0161380 A1 | 6/2013 | Joyce |
| 2013/0162402 A1 | 6/2013 | Amann |
| 2013/0162403 A1 | 6/2013 | Striemer |
| 2013/0162404 A1 | 6/2013 | Striemer |
| 2013/0165809 A1 | 6/2013 | Abir |
| 2013/0211363 A1 | 8/2013 | LaVon et al. |
| 2013/0261409 A1 | 10/2013 | Pathak |
| 2013/0303867 A1 | 11/2013 | Elfstrom |
| 2013/0307570 A1 | 11/2013 | Bosaeus |
| 2013/0310796 A1 | 11/2013 | Zink et al. |
| 2013/0321007 A1 | 12/2013 | Elfstrom |
| 2013/0324955 A1 | 12/2013 | Wong et al. |
| 2013/0338623 A1 | 12/2013 | Kinoshita et al. |
| 2014/0005020 A1 | 1/2014 | LaVon et al. |
| 2014/0005622 A1 | 1/2014 | Wirtz et al. |
| 2014/0014716 A1 | 1/2014 | Joyce et al. |
| 2014/0015644 A1 | 1/2014 | Amann et al. |
| 2014/0015645 A1 | 1/2014 | Striemer et al. |
| 2014/0022058 A1 | 1/2014 | Striemer et al. |
| 2014/0033442 A1 | 2/2014 | Bethea |
| 2014/0062663 A1 | 3/2014 | Bourilkov et al. |
| 2014/0121487 A1 | 5/2014 | Faybishenko et al. |
| 2014/0152442 A1 | 6/2014 | Li |
| 2014/0155850 A1 | 6/2014 | Shah et al. |
| 2014/0155851 A1 | 6/2014 | Ales et al. |
| 2014/0163502 A1 | 6/2014 | Arizti et al. |
| 2014/0188063 A1 | 7/2014 | Nhan et al. |
| 2014/0198203 A1 | 7/2014 | Vardi et al. |
| 2014/0200538 A1 | 7/2014 | Euliano et al. |
| 2014/0241954 A1 | 8/2014 | Phillips et al. |
| 2014/0242613 A1 | 8/2014 | Takeuchi et al. |
| 2014/0242715 A1 | 8/2014 | Nhan et al. |
| 2014/0244644 A1 | 8/2014 | Mashinchi et al. |
| 2014/0266736 A1 | 9/2014 | Cretu-Petra |
| 2014/0292520 A1 | 10/2014 | Carney et al. |
| 2014/0306814 A1 | 10/2014 | Ricci |
| 2014/0329212 A1 | 11/2014 | Ruman et al. |
| 2014/0329213 A1 | 11/2014 | Ruman et al. |
| 2014/0363354 A1 | 12/2014 | Phillips et al. |
| 2014/0371702 A1 | 12/2014 | Bosaeus et al. |
| 2015/0025347 A1 | 1/2015 | Song |
| 2015/0042489 A1 | 2/2015 | LaVon |
| 2015/0045608 A1 | 2/2015 | Karp |
| 2015/0112202 A1 | 4/2015 | Abir |
| 2015/0130637 A1 | 5/2015 | Sengstaken, Jr. |
| 2015/0143881 A1 | 5/2015 | Raut et al. |
| 2015/0150732 A1 | 6/2015 | Abir |
| 2015/0157512 A1 | 6/2015 | Abir |
| 2015/0206151 A1 | 7/2015 | Carney et al. |
| 2015/0209193 A1 | 7/2015 | Ying et al. |
| 2015/0223755 A1 | 8/2015 | Abir |
| 2015/0317684 A1 | 11/2015 | Abir |
| 2016/0008182 A1 | 1/2016 | Prokopuk et al. |
| 2016/0051416 A1 | 2/2016 | Vartiainen et al. |
| 2016/0051417 A1 | 2/2016 | Chiu |
| 2016/0067113 A1 | 3/2016 | Vartiainen et al. |

(56) References Cited

U.S. PATENT DOCUMENTS

| | | |
|---|---|---|
| 2016/0078716 A1 | 3/2016 | Goldman |
| 2016/0080841 A1 | 3/2016 | Bergstrom et al. |
| 2016/0113822 A1 | 4/2016 | Vartiainen et al. |
| 2016/0134497 A1 | 5/2016 | Oloffson Ranta et al. |
| 2016/0136014 A1 | 5/2016 | Arora et al. |
| 2016/0170776 A1 | 6/2016 | Bergstrom et al. |
| 2016/0235603 A1 | 8/2016 | Ehrnsperger et al. |
| 2016/0374868 A1 | 12/2016 | Ettrup Hansen |
| 2017/0108236 A1 | 4/2017 | Guan et al. |
| 2017/0224542 A1 | 8/2017 | Lavon |
| 2017/0224543 A1 | 8/2017 | LaVon et al. |
| 2017/0224550 A1 | 8/2017 | Lavon |
| 2017/0224551 A1 | 8/2017 | LaVon et al. |
| 2017/0224552 A1 | 8/2017 | Lavon |
| 2017/0224553 A1 | 8/2017 | Lavon |
| 2017/0224554 A1 | 8/2017 | Lavon |
| 2017/0252225 A1 | 9/2017 | Arizti et al. |
| 2017/0286977 A1 | 10/2017 | Allen et al. |
| 2017/0312142 A1 | 11/2017 | Lavon |
| 2018/0000660 A1 | 1/2018 | Lavon |
| 2018/0053396 A1 | 2/2018 | Greene |
| 2018/0096290 A1 | 4/2018 | Awad et al. |
| 2018/0147096 A1 | 5/2018 | Lavon et al. |
| 2018/0193202 A1 | 7/2018 | Lavon |
| 2018/0193203 A1 | 7/2018 | Lavon |
| 2019/0180341 A1 | 6/2019 | Matra et al. |
| 2019/0290501 A1 | 9/2019 | Lavon |
| 2020/0069483 A1 | 3/2020 | Lavon et al. |
| 2020/0179185 A1 | 6/2020 | Lavon et al. |
| 2020/0188193 A1 | 6/2020 | Lavon et al. |
| 2020/0188194 A1 | 6/2020 | Lavon et al. |
| 2020/0197236 A1 | 6/2020 | Lavon et al. |
| 2020/0206044 A1 | 7/2020 | Lavon et al. |
| 2020/0222252 A1 | 7/2020 | Lavon et al. |

FOREIGN PATENT DOCUMENTS

| | | | |
|---|---|---|---|
| EP | 1542635 | B1 | 4/2012 |
| EP | 2491899 | B1 | 7/2014 |
| JP | 09187431 | A | 7/1997 |
| JP | 2002022687 | A1 | 1/2002 |
| JP | 2002143199 | A1 | 5/2002 |
| JP | 2003190209 | A1 | 7/2003 |
| JP | 2004041697 | | 2/2004 |
| JP | 2004230135 | A1 | 8/2004 |
| JP | 2006296566 | A1 | 11/2006 |
| WO | WO199516746 | A1 | 6/1995 |
| WO | WO199934841 | | 7/1999 |
| WO | WO 0197466 | | 12/2001 |
| WO | WO2010123364 | A1 | 10/2010 |
| WO | WO2010123425 | A1 | 10/2010 |
| WO | WO2011013874 | A1 | 2/2011 |
| WO | WO2012084925 | A1 | 6/2012 |
| WO | WO2012126507 | A1 | 9/2012 |
| WO | 2012166765 | A1 | 12/2012 |
| WO | WO2013-003905 | | 1/2013 |
| WO | WO 2013016765 | | 2/2013 |
| WO | WO2013016765 | A1 | 2/2013 |
| WO | WO2013061963 | A1 | 5/2013 |
| WO | WO2013-091728 | | 6/2013 |
| WO | WO2013-095226 | | 6/2013 |
| WO | WO2013-095230 | | 6/2013 |
| WO | WO2013091707 | A1 | 6/2013 |
| WO | WO2013095222 | A1 | 6/2013 |
| WO | WO2013095231 | | 6/2013 |
| WO | WO2013-097899 | | 7/2013 |
| WO | WO2013181436 | A1 | 12/2013 |
| WO | WO2013185419 | A1 | 12/2013 |
| WO | WO2013189284 | A1 | 12/2013 |
| WO | WO2014035302 | A1 | 3/2014 |
| WO | WO2014035340 | A1 | 3/2014 |
| WO | WO2014122169 | A1 | 8/2014 |
| WO | WO2014-137671 | | 9/2014 |
| WO | WO2014-146693 | | 9/2014 |
| WO | WO2014-146694 | | 9/2014 |
| WO | WO2014148957 | A1 | 9/2014 |
| WO | WO2014-177200 | | 11/2014 |
| WO | WO2014-177203 | | 11/2014 |
| WO | WO2014-177204 | | 11/2014 |
| WO | WO2014-177205 | | 11/2014 |
| WO | WO2014-178763 | | 11/2014 |
| WO | WO2014192978 | A1 | 12/2014 |
| WO | WO2015-003712 | | 1/2015 |
| WO | WO2015-068124 | | 5/2015 |
| WO | WO2015-102084 | | 7/2015 |
| WO | WO2015102084 | A1 | 7/2015 |
| WO | WO2015102085 | | 7/2015 |
| WO | WO2015102085 | A1 | 7/2015 |

OTHER PUBLICATIONS

All Office Actions U.S. Appl. No, 13/483,456.
All Office Actions U.S. Appl. No. 15/497,367.
All Office Actions U.S. Appl. No. 15/497,541.
All Office Actions U.S. Appl. No. 15/497,574.
All Office Actions U.S. Appl. No. 15/497,641.
All Office Actions U.S. Appl. No. 15/497,674.
All Office Actions U.S. Appl. No. 15/497,735.
All Office Actions U.S. Appl. No. 15/497,823.
All Office Actions U.S. Appl. No. 15/653,821.
All Office Actions U.S. Appl. No. 15/705,996.
All Office Actions U.S. Appl. No. 15/916,827.
All Office Actions U.S. Appl. No. 15/916,854.
All Office Actions U.S. Appl. No. 15/931,818.
All Office Actions U.S. Appl. No. 16/360,125.
All Office Actions U.S. Appl. No. 16/438,512.
All Office Actions U.S. Appl. No. 16/675,636.
All Office Actions U.S. Appl. No. 16/794,371.
All Office Actions U.S. Appl. No. 16/796,002.
All Office Actions U.S. Appl. No. 16/799,886.
All Office Actions U.S. Appl. No. 16/807,262.
All Office Actions U.S. Appl. No. 16/812,812.
All Office Actions U.S. Appl. No. 16/830,352.
All Office Actions and Responses, U.S. Appl. No. 13/483,463.
All Office Actions and Responses, U.S. Appl. No. 14/455,088.
All Office Actions, U.S. Appl. No. 16/296,329.
All Office Actions, U.S. Appl. No. 16/360,477.
All Office Actions, U.S. Appl. No. 15/656,217.
All Office Actions, U.S. Appl. No. 13/483,463.
All Office Actions, U.S. Appl. No. 14/455,088.
All Office Actions, U.S. Appl. No. 15/134,035.
All Office Actions, U.S. Appl. No. 15/879,971.
Amendment for U.S. Appl. No. 13/483,463 dated Aug. 21, 2014.
International Search Report, PCT/US2014/050083, dated Oct. 28, 2014, 8 pages.
International Search Report, PCT/US2017/019326, dated Sep. 4, 2018, 6 pages.
Non-Final Rejection for U.S. Appl. No. 13/483,463 dated May 21, 2014.
PCT International Search Report and Written Opinion, PCT/US2012/039943 dated Aug. 23, 2012.
PCT International Search Report, PCT/US2012/039940 dated May 30, 2012.
United States Consumer Product Safety Commission, "Small Parts for Toys and Children's Products Business Guidance", https://www.cpsc.gov/Business--Manufacturing/Business-Education/Business-Guidance/Small-Parts-for-Toys-and-Childrens-Products, 7 pages.
U.S. Appl. No. 15/931,818, filed May 14, 2020, Gary Dean LaVon et al.

* cited by examiner

ABSORBENT ARTICLES COMPRISING SENSORS

FIELD

In general, embodiments of the present disclosure relate to sensors for use with absorbent articles. In particular, embodiments of the present disclosure relate to sensors designed to lower the potential for accidental choking.

BACKGROUND OF INVENTION

The art discloses many different types of sensors that are integral with an absorbent article (e.g., placed internal of the garment-facing layer or fixed to interior or exterior surfaces of the garment-facing layer). One of the problems with designs having an internal sensor is that most are throw away sensors, i.e. the sensor is a single-use design disposed within the absorbent article primarily because it is undesirable to reuse them once they become contaminated with fecal waste and urine. Such an approach can be expensive given the need to incorporate a sensor into every absorbent article, e.g. a diaper. In addition, products that rely on an electrical circuit as the means for indication on the inside of the product can also expose the wearer to low voltage electrical current.

Alternatively, the sensor may be placed external of the garment-facing layer, but still integral with the absorbent article. One of the problems with a sensor fixed to the external surface of the garment-facing layer is creating a means for locating the sensor appropriately and then holding or attaching the sensor to the garment-facing layer.

Another problem with a sensor fixed to the external surface of the garment-facing layer is the potential of the sensor to present potential for accidental choking. This is also a challenge of sensors designed to be reusable, whether disposed internally of the absorbent article or externally due to their removable/reusable nature.

It is a goal to overcome the challenges mentioned above. Particularly, one goal of the present disclosure is to locate the sensor in or on an absorbent article, either internally or externally, or on an auxiliary article, such that the potential for creating a choking hazard is greatly reduced. It is also a goal of the invention to size and/or shape the sensor to decrease the potential for creating a choking hazard.

BRIEF DESCRIPTION OF THE DRAWINGS

FIGS. 7A-C illustrate an ultrasonic-type sensor, according to embodiments of the present disclosure.

DETAILED DESCRIPTION

Figure 1A:
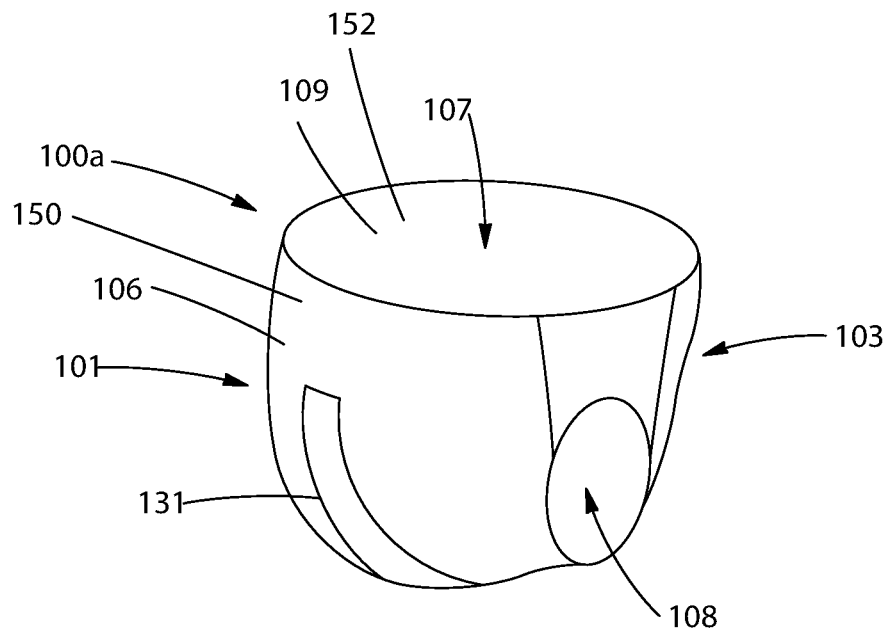
FIG. 1A illustrates a pant-type absorbent article with a sensor in the front, according to embodiments of the present disclosure.

Embodiments of the present disclosure illustrate various absorbent articles comprising various sensors and/or auxiliary articles comprising various sensors that may be used with various absorbent articles to make a sensor system. And, as described above, the sensors of the present disclosure are located on or in an article and/or designed to prevent or reduce the risk of choking.

Absorbent Article

The absorbent article may be one for personal wear, including but not limited to diapers, training pants, feminine hygiene products, incontinence products, medical garments, surgical pads and bandages, other personal care or health care garments, and the like. Various materials and methods for constructing absorbent articles such as diapers and pants are disclosed in U.S. Pub. Nos. 2011-0041999, 2010-0228211, 2008-0208155, and 2009-0312734.

The sensor may be discrete from or integral with the absorbent article. The absorbent article may comprise sensors that can sense various aspects of the absorbent article associated with insults of bodily exudates such as urine and/or BM (e.g., the sensor may sense variations in temperature, humidity, presence of ammonia or urea, various vapor components of the exudates (urine and feces), changes in moisture vapor transmission through the absorbent articles garment-facing layer, changes in translucence of the garment-facing layer, color changes through the garment-facing layer, etc.). Additionally, the sensors my sense components of urine, such as ammonia or urea and/or byproducts resulting from reactions of these components with the absorbent article. The sensor may sense byproducts that are produced when urine mixes with other components of the absorbent article (e.g., adhesives, agm, etc.). The components or byproducts being sensed may be present as vapors that may pass through the garment-facing layer. It may also be desirable to place reactants in the diaper that change state (e.g. color, temperature, etc.) or create a measurable byproduct when mixed with urine. The sensor may also sense changes in pH, pressure, odor, the presence of gas, blood, a chemical marker or a biological marker or combinations thereof.

The sensor may be removably integrated with the absorbent article with hook and loops fasteners, adhesives, thermal bonds, mating fasteners like snaps or buttons, or may be disposed in pockets, recesses or void spaces built into the absorbent article, or combinations thereof. Many of these integration means enable removal of and/or attachment of the sensor from or to the absorbent article. The absorbent article may further comprise graphics for the purpose of properly locating the sensor. The graphics may appear as an outline of the sensor, may symbolize a target, may be a different color than the surrounding area of the article, may state, "Place sensor here," may correspond with instructions from a manual, or may be combination of one or more of these approaches.

Regarding pockets, it may be desirable to form a pocket with or adjacent to the wearer-facing layer or garment-facing layer. In some embodiments, a pocket may be formed by joining an additional material (e.g., a nonwoven strip) to the interior or exterior surface of the garment-facing layer. When joined to the interior surface of the garment facing layer, it may be desirable to position an open edge (to be the pocket opening) of the sheet to be coterminous or adjacent to an edge of the waist opening such that there is no need to make a cut in the garment facing layer for inserting the sensor into the pocket opening.

When joined to the exterior surface of the garment-facing layer, the non-open edges of the sheet may be permanently joined, while an open edge (to be the pocket opening) may be refastenably joined to the garment-facing layer.

FIGS. 1A-2C illustrate acceptable absorbent articles, each with one or more sensors. For clarity, FIGS. 1A-2C do not illustrate all details of the sensors or of the absorbent articles. Each sensor and/or absorbent article in FIGS. 1A-2C can be any embodiment of the present disclosure.

FIG. 1A illustrates an outside perspective view of a front 101 and a side 103 of a pant-type absorbent article 100A formed for wearing. The pant-type absorbent article 100A may include a waist opening 107, a leg opening 108, an exterior surface (garment-facing) 106 formed by a garment-facing layer 150A sometimes referred to as the garment-facing layer, and an interior surface (wearer-facing) 109 formed by a wearer-facing layer 152A sometimes referred to as the wearer-facing layer. The absorbent article 100A may include a longitudinally oriented sensor 131 disposed in the front 101.

The wearer-facing layer 152A may be a layer of one or more materials that forms at least a portion of the inside of the front-fastenable wearable absorbent article and faces a wearer when the absorbent article 100A is worn by the wearer. In FIG. 1A, a portion of the wearer-facing layer 152A is illustrated as broken-away, in order to show the garment-facing layer 150A. A wearer-facing layer is sometimes referred to as a topsheet. The wearer-facing layer 152A is configured to be liquid permeable, such that bodily fluids received by the absorbent article 100A can pass through the wearer-facing layer 152A to the absorbent material 154A. In various embodiments, a wearer-facing layer can include a nonwoven material and/or other materials as long as the materials are liquid permeable over all or part of the wearer-facing layer.

The absorbent material 154A may be disposed subjacent to the wearer-facing layer 152A and superjacent to the garment-facing layer 150A, in at least a portion of the absorbent article 100A. In some embodiments, an absorbent material of an absorbent article is part of a structure referred to as an absorbent core. The absorbent material 154A may be configured to be liquid absorbent, such that the absorbent material 154A can absorb bodily fluids received by the absorbent article 100A. In various embodiments, an absorbent material can include cellulosic fibers (e.g., wood pulp fibers), other natural fibers, synthetic fibers, woven or nonwoven sheets, scrim netting or other stabilizing structures, superabsorbent material, foams, binder materials, adhesives, surfactants, selected hydrophobic materials, pigments, lotions, odor control agents or the like, as well as combinations thereof. The absorbent structure may comprise one or more storage layers and one or more surge management layers. A pair of containment flaps, elasticated leg cuffs, may form a portion of the interior surface of the absorbent assembly for inhibiting the lateral flow of body exudates.

The garment-facing layer 150A may be a layer formed of one or more materials that form at least a portion of an outside of the front-fastenable wearable absorbent article and may face a wearer's garments when the absorbent article 100A is worn by the wearer. A garment-facing layer is sometimes referred to as a backsheet. The garment-facing layer 150A may be configured to be liquid impermeable, such that bodily fluids received by the absorbent article 100A cannot pass through the garment-facing layer 150A. In various embodiments, a garment-facing layer can include a nonporous film, a porous film, a woven material, a non-woven fibrous material or combinations thereof. The outer cover may also be stretchable, extensible, and in some embodiments it may be elastically extensible or elastomeric. The garment-facing layer 150A may also be vapor permeable and yet liquid impervious.

Throughout the present disclosure, a reference to a pant-type absorbent article can refer to an embodiment that is side-fastenable or to an embodiment without fasteners. A reference to a pant-type absorbent article refers to an article having preformed waist and/or leg openings. Thus, each embodiment of an absorbent article of the present disclosure that is described as pant-type can be configured in any of these ways, as will be understood by one of ordinary skill in the art.

Figure 1B:
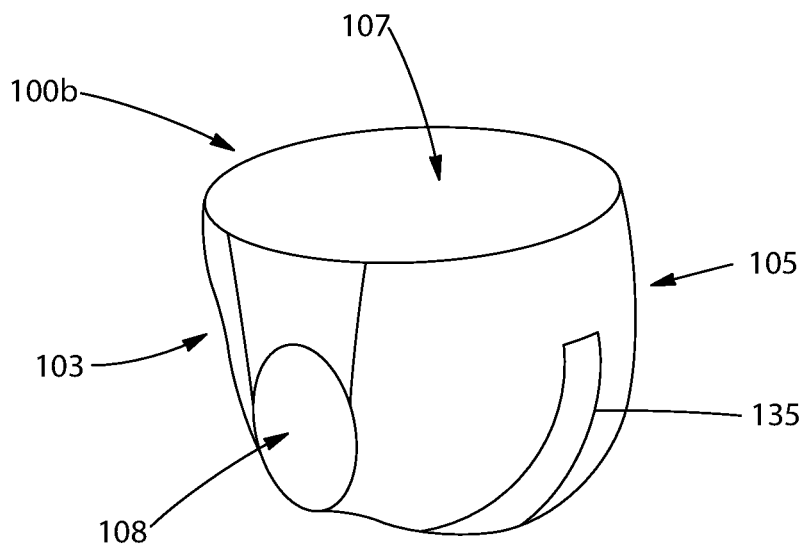
FIG. 1B illustrates a pant-type absorbent article with a sensor in the back, according to embodiments of the present disclosure.

FIG. 1B illustrates an outside perspective view of a side 103 and a back 105 of a pant-type absorbent article 100B formed for wearing. The pant-type absorbent article 100B may include a waist opening 107 and a leg opening 108. Absorbent article 100B may include a longitudinally oriented sensor 135 in the back 105.

Figure 1C:
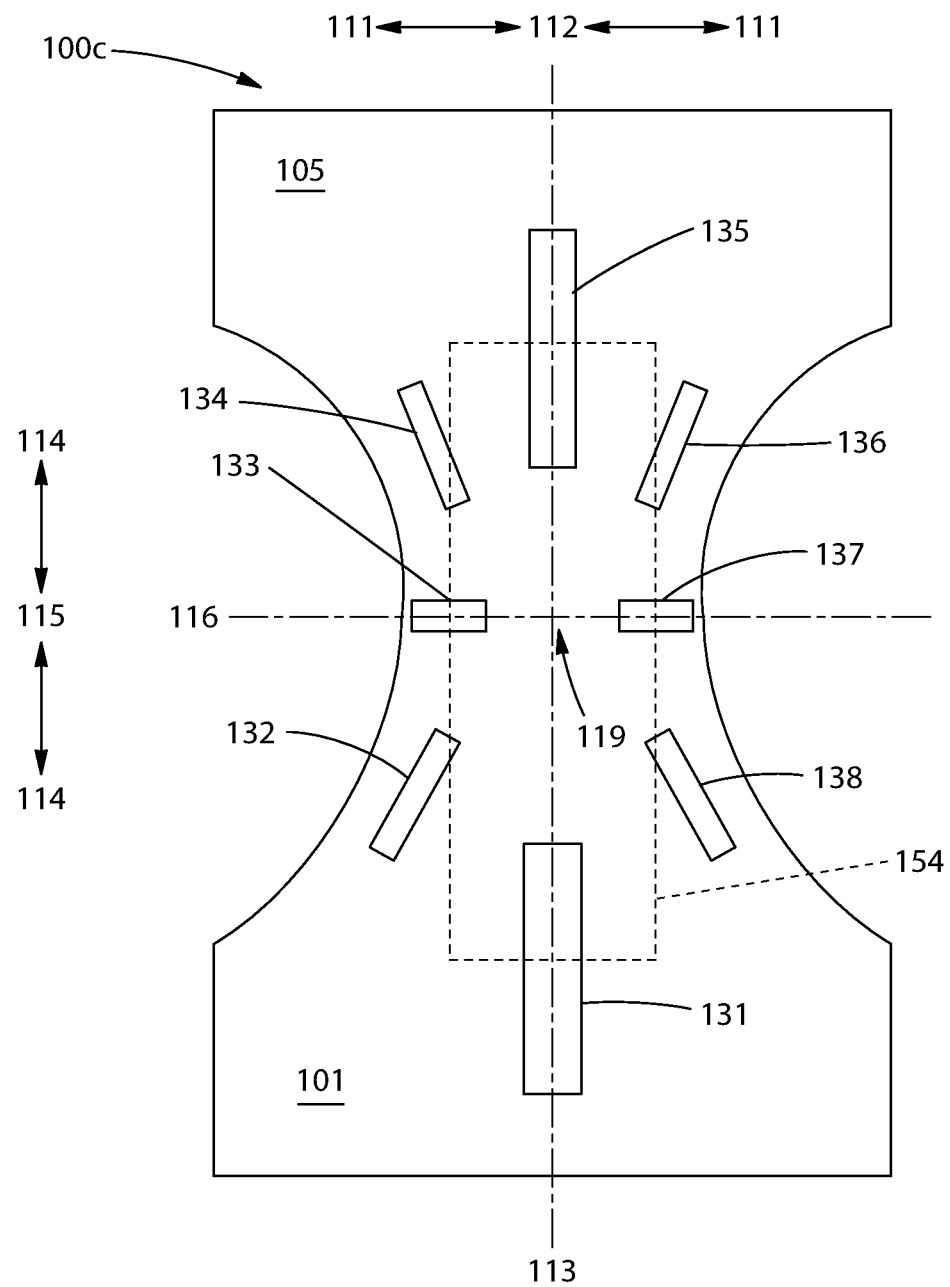
FIG. 1C illustrates a pant-type absorbent article with a plurality of sensors, according to embodiments of the present disclosure.

FIG. 1C illustrates an outside plan view of a pant-type absorbent article 100C laid out flat. The absorbent article 100C may include a front 101 and a back 105, separated by a lateral centerline 116.

In FIG. 1C, a longitudinal centerline 113 and the lateral centerline 116 provide lines of reference for referring to relative locations of the absorbent article 100C. When a first location 112 is nearer to the longitudinal centerline 113 than a second location 111, the first location 112 can be considered laterally inboard to the second location 111. Similarly, the second location 111 can be considered laterally outboard from the first location 112. When a third location 115 is nearer to the lateral centerline 116 than a fourth location 114, the third location 115 can be considered longitudinally inboard to the fourth location 114. Also, the fourth location 114 can be considered longitudinally outboard from the third location 115.

A reference to an inboard location, without a lateral or longitudinal limitation, refers to a location of the absorbent article 100C that is laterally inboard and/or longitudinally inboard to another location. In the same way, a reference to an outboard location, without a lateral or longitudinal limitation, refers to a location of the absorbent article 100C that is laterally outboard and/or longitudinally outboard from another location.

Inboard and outboard can also be understood with reference to a center of an absorbent article. The longitudinal centerline 113 and the lateral centerline 116 cross at a center 119 of the absorbent article 100C. When one location is nearer to the center 119 than another location, the one location can be considered inboard to the other location. The one location can be inboard laterally, or longitudinally, or both laterally and longitudinally. The other location can be considered outboard from the one location. The other location can be outboard laterally, or longitudinally, or both laterally and longitudinally.

FIG. 1C includes arrows indicating relative directions for laterally outboard 111 relative to 112, laterally inboard 112 relative to 111, longitudinally outboard 114 relative to 115, and longitudinally inboard 115 relative to 114, each with respect to the absorbent article 100C. Throughout the present disclosure, a reference to a longitudinal dimension, measurement, line, or direction refers to a dimension, measurement, line, or direction that is substantially or completely parallel to the longitudinal centerline 113 and a reference to a lateral dimension, measurement, line, or direction refers to a dimension, measurement, line, or direction that is substantially or completely parallel to the lateral centerline 116. The terminology for describing relative locations, as discussed above, is used for absorbent articles throughout the present disclosure. This terminology can also be similarly applied to various other absorbent articles, as will be understood by one of ordinary skill in the art.

The absorbent article 100C may include a number of sensors in various exemplary locations and orientations. The absorbent article 100C may include a longitudinally oriented sensor such as sensor 131 and 135, along the longitudinal centerline 113 in the front 101 and/or back 105. The front 101 and/or back 105 may include at least one angled sensor such as sensors 132, 134, 136 and 138 oriented at an angle between the longitudinal centerline 113 and the lateral centerline 116. The absorbent article 100C may include one or more laterally oriented sensors such as sensors 133 and 137 along the lateral centerline 116.

In the absorbent article 100C, the sensors may be oriented substantially radially out from the center 119. However, in addition to the locations and orientations illustrated in FIG. 1C, a sensor of the present disclosure can be disposed in various alternate locations and orientations relative to an absorbent article. As an example, a sensor can be disposed in a pant-type absorbent article at a location relative to a pee point for a wearer of the absorbent article.

Figure 2A:
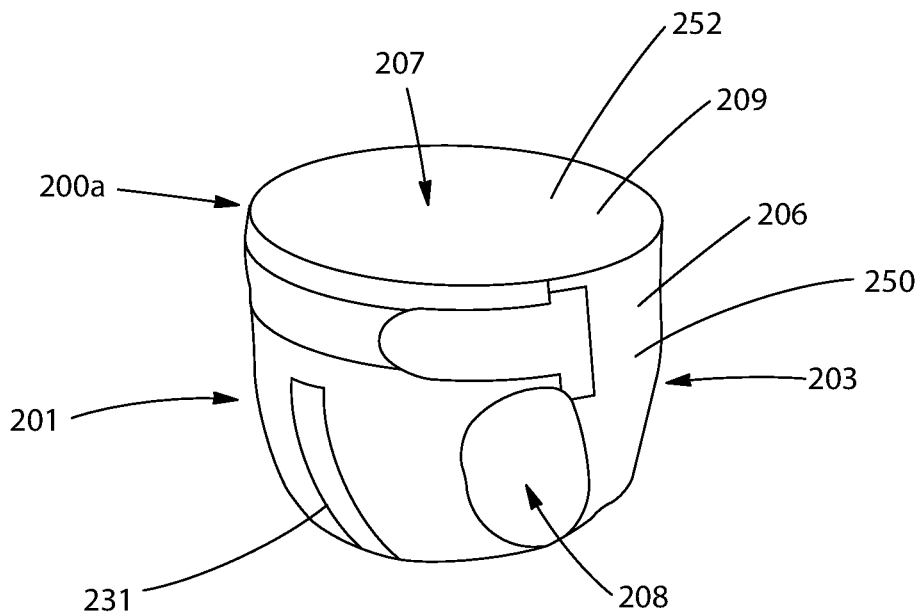
FIG. 2A illustrates a front-fastenable absorbent article with a sensor in the front, according to embodiments of the present disclosure.

FIG. 2A illustrates an outside perspective view of a front 201 and a side 203 of a front-fastenable absorbent article 200A formed for wearing. The front-fastenable absorbent article 200A may include a waist opening 207 and a leg opening 208. The absorbent article 200A may include a longitudinally oriented sensor 231 disposed in the front 201.

While the present disclosure refers to front-fastenable absorbent articles, the present disclosure also contemplates alternate embodiments of absorbent articles wherein the absorbent articles are rear-fastenable. Thus, each embodiment of an absorbent article of the present disclosure that is described as front-fastenable can also be configured to be rear-fastenable.

Figure 2B:
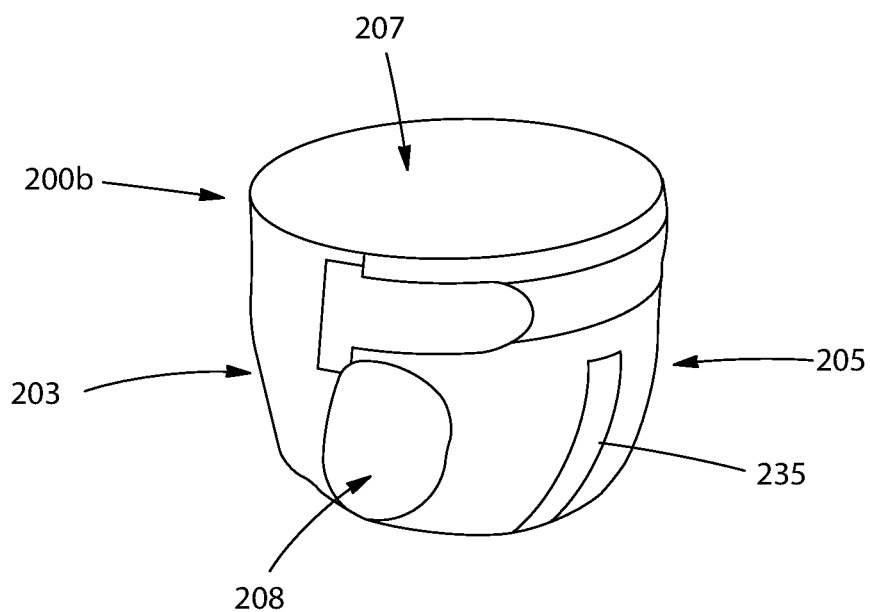
FIG. 2B illustrates a front-fastenable absorbent article with a sensor in the back, according to embodiments of the present disclosure.

FIG. 2B illustrates an outside perspective view of a side 203 and a back 205 of a front-fastenable absorbent article 200B formed for wearing. The front-fastenable absorbent article 200B may include a waist opening 207 and a leg opening 208. The absorbent article 200B may include a longitudinally oriented sensor 235 in the back 205.

Figure 2C:
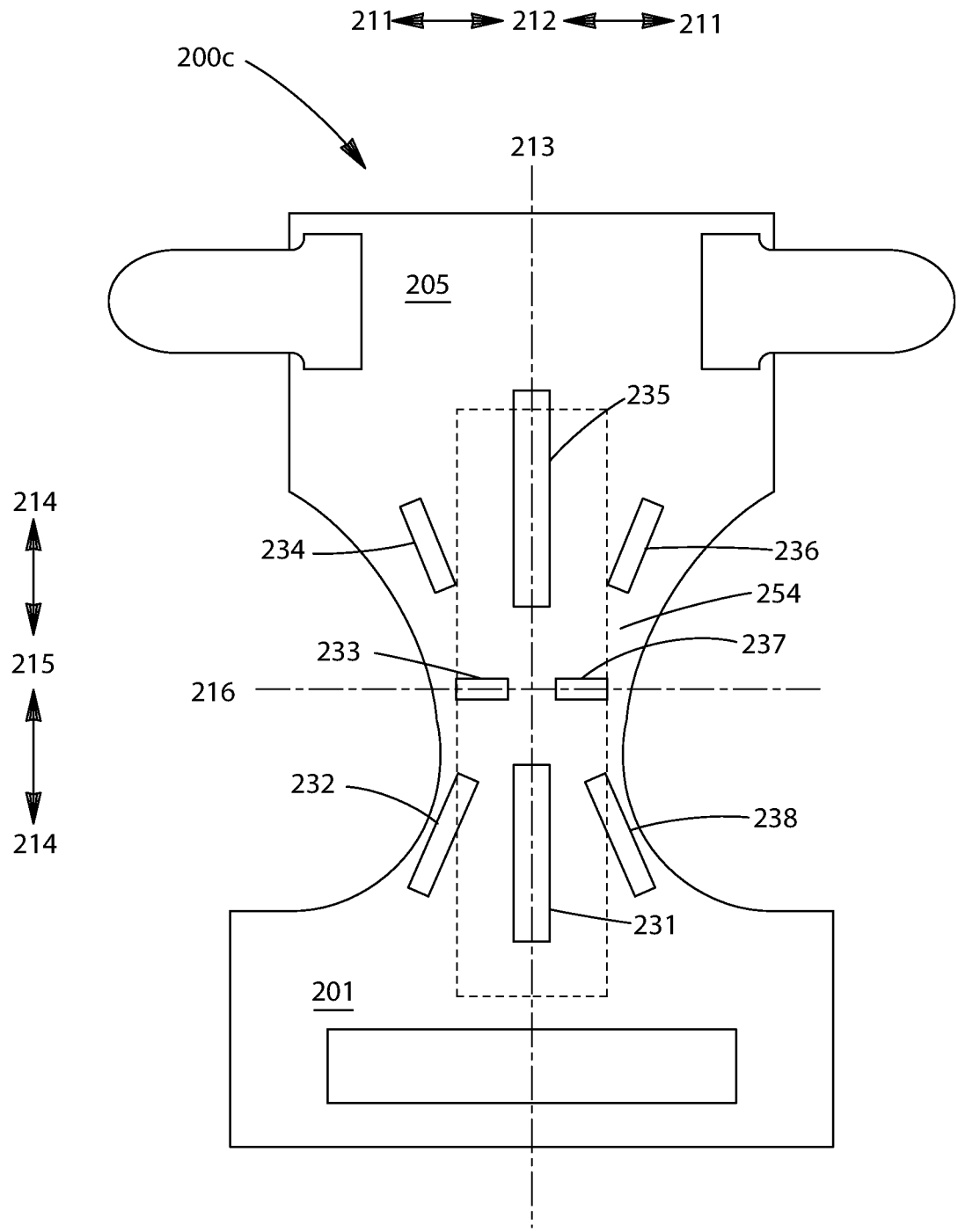
FIG. 2C illustrates a front-fastenable absorbent article with a plurality of sensors, according to embodiments of the present disclosure.

FIG. 2C illustrates an outside plan view of a front-fastenable absorbent article 200C laid out flat. The absorbent article 200C may include a front 201, a back 205, a longitudinal centerline 213, and a lateral centerline 216, an exterior surface 206, and an interior (wearer-facing) surface 209.

The absorbent article 200C may include a number of sensors in various exemplary locations and orientations. The absorbent article 200C may include longitudinally oriented sensors such as sensors 231 and 235, along the longitudinal centerline 213 in the front 201 and/or back 205. The front 201 and/or back 205 may include angled sensors such as sensors 232, 234, 236 and 238 oriented at an angle between the longitudinal centerline 213 and the lateral centerline 216. The absorbent article 200C may include laterally oriented sensors such as sensors 233 and 237 along the lateral centerline 216.

In the absorbent article 200C, the sensors may be oriented substantially radially out from the center 219. However, in addition to the locations and orientations illustrated in FIG. 2C, a sensor of the present disclosure can be disposed in various alternate locations and orientations in an absorbent article. As an example, a sensor can be disposed in a front-fastenable absorbent article at a location relative to a pee point of a wearer of the article.

Figure 3:
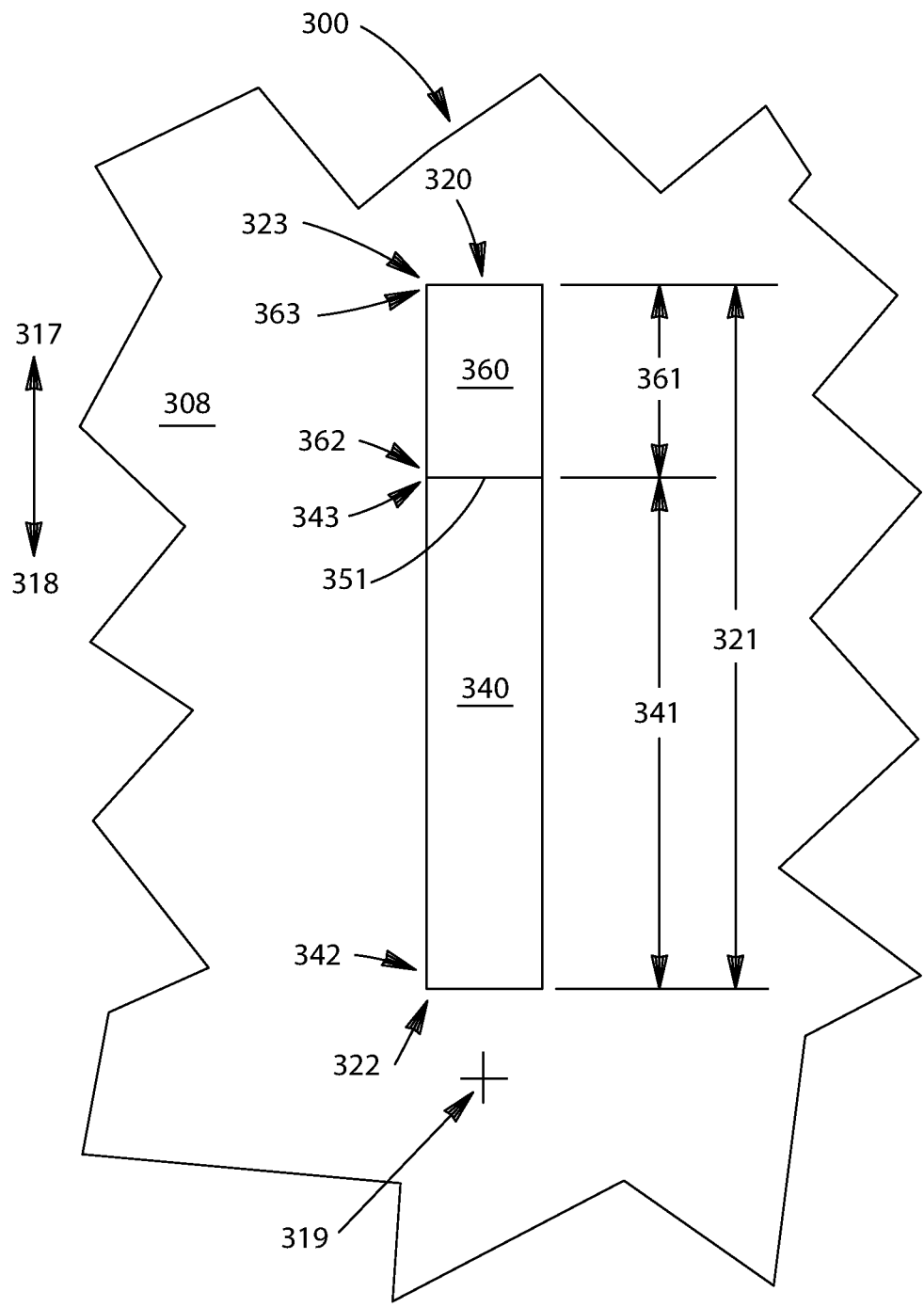
FIG. 3 illustrates a portion of an absorbent article with a sensor having a first sensing area and a second sensing area, according to embodiments of the present disclosure.
Figure 4:
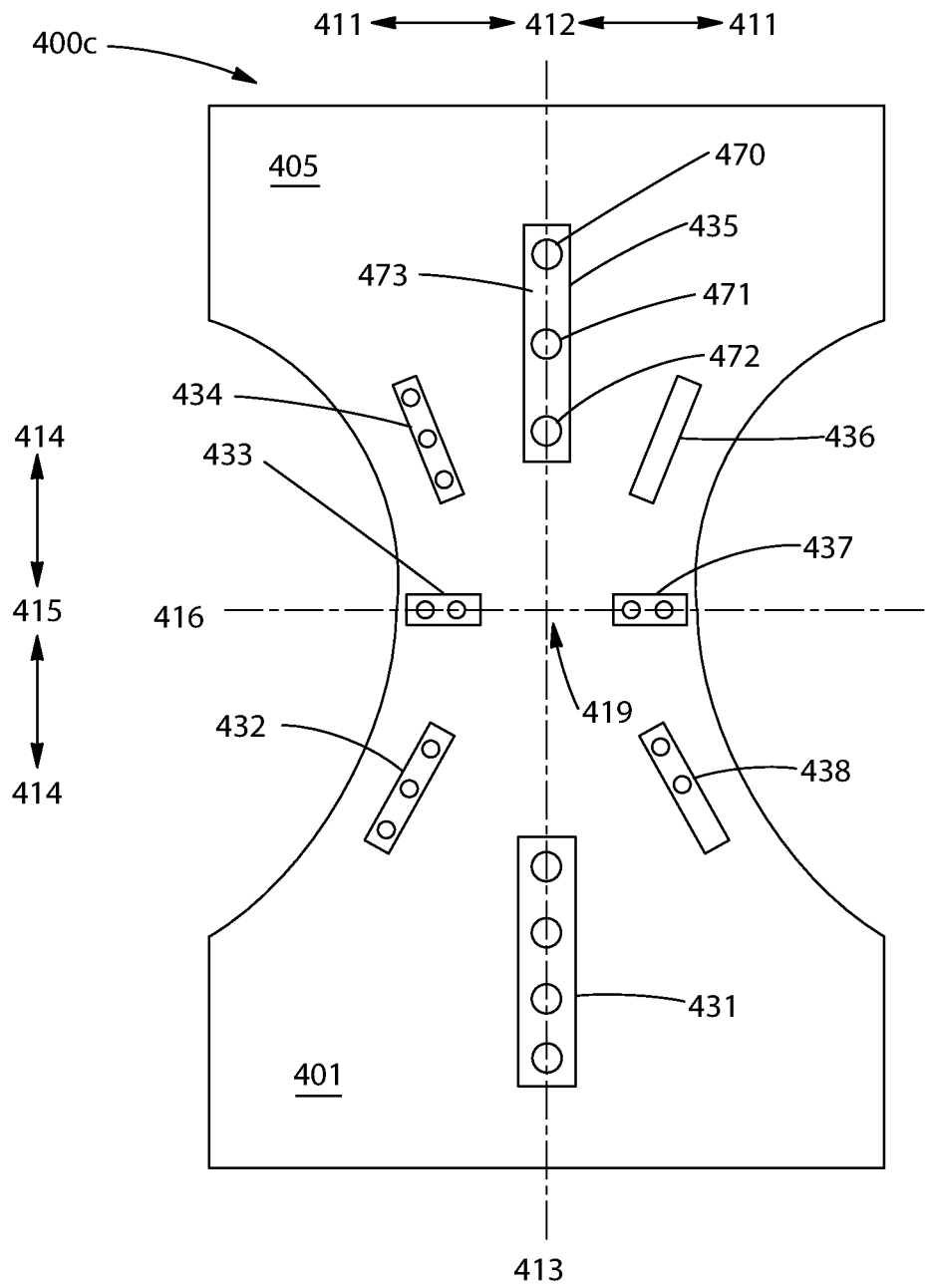
FIG. 4 illustrates a pant-type absorbent article with a plurality of sensors, according to embodiments of the present disclosure.

FIG. 3 illustrates an outside plan view of a portion 308 of an absorbent article 300 laid out flat. In various embodiments, the absorbent article 300 can be an absorbent article, such as a pant-type absorbent article or a front-fastenable absorbent article. In FIG. 3, outside edges of the portion 308 are broken lines, since the portion 308 is illustrated as separate from the rest of the absorbent article 300. For reference, FIG. 3 illustrates a center 319 of the absorbent article 300 and arrows indicating relative directions for outboard 317 and inboard 318 for the absorbent article 300.

The portion 308 of the absorbent article 300 may include a sensor 320. The sensor 320 may be disposed offset from the center 319. In various embodiments, one or more parts of a sensor can be disposed near, at, or overlapping a center of an absorbent article. For example, a single sensing area can extend from a front of an absorbent article, through the center of the absorbent article, to the back of the absorbent article. In such an embodiment, a farthest inboard point along the sensing area can be considered an inboard end of two sensors.

The sensor 320 may include an inboard end 322 and an outboard end 323. The sensor 320 has an overall sensor length 321, measured along the sensor 320 from the inboard end 322 to the outboard end 323. The sensor 320 may have an overall shape that is substantially elongated and substantially rectangular. The sensor 320 may have a substantially uniform width along the entire overall sensor length 321. It may be desirable that the sensor, or a portion of the sensor, has a bending stiffness of less than about 1000 N/m, 600 N/m, or 400 N/m (as determined by ASTM D 790-03) to keep it from irritating the wearer. It may alternatively or additionally be desirable to design the sensor, or a portion of the sensor, to have a bending modulus (N/m2) of less than 2.0 E+09, 1.0 E+08, or 1.0 E+06.

In various embodiments a sensor can have an overall shape that is more or less elongated. In some embodiments, all or part of a sensor may be linear, curved, angled, segmented, or any regular or irregular geometric shape (such as a circle, square, rectangle, triangle, trapezoid, octagon, hexagon, star, half circle, a quarter circle, a half oval, a quarter oval, a radial pattern, etc.), a recognizable image (such as a letter, number, word, character, face of an animal, face of a person, etc.), or another recognizable image (such as a plant, a car, etc.), another shape, or combinations of any of these shapes. Also, in various embodiments, an indicator can have varying widths over all or part of its length.

The sensor 320 may include one or more sensing areas for example, a first sensing area 340 and a second sensing area 360. In various embodiments, a sensor can include three or more sensing areas.

The first sensing area 340 may include a first area inboard end 342, a first area outboard end 343, and a first area overall length 341 measured along the first sensing area 340 from the first area inboard end 342 to the first area outboard end 343. The first sensing area 340 may have an overall shape that is substantially elongated and substantially rectangular. The first sensing area 340 may have a substantially uniform width along the entire first area overall length 341. However, in some embodiments, an sensing area can have various shapes and various widths over all or part of its length, as described above in connection with the sensor.

In addition to the first sensing area 340, the sensor 320 may include a second sensing area 360. In the embodiment of FIG. 3, the second sensing area 360 is outboard 317 from the first sensing area 340. The second sensing area 360 may include a second area inboard end 362, a second area outboard end 363, and a second area overall length 361 measured along the second sensing area 360 from the second area inboard end 362 to the second area outboard end 363. In the embodiment of FIG. 3, the second area overall length 361 is less than the first area overall length 341. In some embodiments, a second area overall length can be equal to a first area overall length or greater than a first area overall length.

The second sensing area 360 may have an overall shape that is substantially elongated and substantially rectangular. The second visual fullness sensing area 360 may have a substantially uniform width along the entire second area overall length 361.

Auxiliary Article Structure

One or more sensors may be used with an auxiliary article. The auxiliary article may be a durable, washable, reusable garment designed to fit over an absorbent article. The auxiliary article may be made of various materials, including rayon, nylon, polyester, various polyolefins, spandex, cotton, wool, flax, or combinations thereof.

The auxiliary article may comprise the sensor between two of its layers. A pocket may be formed in or on the inner or outer surface of the auxiliary article. A window may be formed through one or more of the layers of the auxiliary article to provide for better communication between the sensor and the absorbent article.

The sensor may be discrete or integral with the auxiliary article. Integral embodiment may comprise a sensor that can be washed.

The sensor may be removably integrated with the auxiliary article with hook and loops fasteners, adhesives, thermal bonds, mating fasteners like snaps or buttons, or may be disposed in pockets, recesses or void spaces built into the auxiliary article, or combinations thereof. Many of these integration means enable removal of and/or attachment of the sensor from or to the auxiliary article. The auxiliary article may be designed to receive an absorbent article for example an insert. Examples of such auxiliary article chassis that may be desired are disclosed in U.S. Pat. No. 7,670,324 and U.S. Pub. Nos. 2010-0179500, 2010-0179496, 2010-0179501, 2010-0179502, and 2010-0179499.

The auxiliary article may be in the form of a pant-like garment for example children's underwear. The sensors may be adapted to work collaboratively with other forms of children's clothing for example jeans, shorts, overalls, etc. For example, the sensor may be part of an iron-on kit, such that the sensor may be ironed onto a pair of regular underpants or panties. Alternatively, the kit may comprise a patch (or several patches) that can be ironed on or otherwise adhered to the underwear so that the sensor could be removably be attached to the patch. In this embodiment, the sensor could be used from garment to garment.

The sensor disposition and/or patterns disclosed above for the absorbent article can also apply to the auxiliary article.

Throughout the present disclosure, a reference to a pant-type auxiliary article can refer to an embodiment that is side-fastenable or to an embodiment without fasteners. A reference to a pant-type auxiliary article refers to an article having preformed waist and/or leg openings. Thus, each embodiment of an auxiliary article of the present disclosure that is described as pant-type can be configured in any of these ways, as will be understood by one of ordinary skill in the art.

The auxiliary article may also come in the form of a front-fastenable auxiliary article. While the present disclosure refers to front-fastenable auxiliary articles, the present disclosure also contemplates alternate embodiments of absorbent articles, as described herein, wherein the auxiliary articles are rear-fastenable. Thus, each embodiment of an absorbent article of the present disclosure that is described as front-fastenable can also be configured to be rear-fastenable.

The auxiliary article (whether front or rear-fastenable or pant-type) may comprise stretchable materials, extensible materials, elastically extensible materials or combinations thereof disposed at or adjacent the waist and leg openings to provide the extension necessary for application and body conforming fit in use. The front fastening auxiliary article may further comprise and overall stretchable, extensible or elastically extensible layer forming that provides a snug fit of the auxiliary article to the absorbent article.

Sensor Structure

As used in this application, the term "sensor" (e.g., 435) refers not only to the elements (e.g., 470, 471, and 472) responsible for detecting a stimulus and signaling such detection (via impulse), but also includes the housing or carrier layer or substrate (e.g., 473) around such element(s). A "sensor" may include a carrier layer (e.g., 473) with multiple elements (e.g., 470, 471, and 472) capable of detecting one or more stimuli; and, the multiple elements may create multiple locations capable of detecting one or more stimuli. The sensors of the present disclosure may form a part of a sensor system capable of monitoring urine and/or fecal insults. The system that may take on a variety of configurations which are determined by the means in which the presence of urine and/or feces is detected. After detection of urine and/or feces, the system may inform a caregiver and/or a child by generating a notification. The notification may be and auditory signal, an olfactory signal, a tactile signal or a visual signal. It is understood that the system may comprise a device for sending a wireless signal to a remote receiver which may in turn result in an auditory signal, visual signal, tactile signal or other sensory signal and/or combinations thereof.

Manufacturing the sensor independent of the primary disposable absorbent article enables utilization of more expensive components and delivery of more sophisticated sensor technology. For example, internal sensors and/or sensors that are part of the absorbent article may require a built in power source that needs to last through the storage, shelf-life and usage of the absorbent article it is incorporated into. Not to mention, that integrated sensors can introduce significant cost. To offset cost, more simple sensors may be utilized but the functionality and reliability of such cheap sensors would suffer. Stand alone sensors disposed exteriorly of the absorbent article do not have these limitations and could include a means for replacing the power supply or could be rechargeable.

The sensor may be washable and thus created in a water-tight casing or coating capable of withstanding temperatures of greater than about 185° F., or greater than about 200° F.

Various sensors may be used, including inductive, capacitive, ultra sonic, optical, moisture, humidity, chemical, temperature, electromagnetic and combinations thereof.

Sensor Size/Dimension

Whether the sensor is used with an absorbent article (e.g., such that it is joined to the garment-facing layer or wearer-facing layer or placed in a pocket formed by a portion of the absorbent article) or the sensor is used with an auxiliary article (e.g., such that it is joined to an interior or exterior surface or placed in a pocket formed by a portion of the auxiliary article), there may be a desire to design the sensor such that it does not present a potential physical hazard challenge in the event the child were to detach the sensor from the article. A typical physical hazard that such an event could present is choking.

To minimize the choking potential the width of the sensor (which includes its carrier layer) may be designed to be greater than 1.25 inches. If the width of the sensor apparatus is less than 1.25 inches it may be desirable to design it to have a length of greater than 2.25 inches. Other desirable embodiments may be as sensor having a width greater than 1.5 inches and/or a length greater than 3 inches.

Furthermore, it may be desirable that the ends of the sensor (at the narrowest portion) are not curved (convex) because such a curve can open the airway and allow the device to slide further into the windpipe. If a curve is desired, however, it may be desired that it have a radius of curvature greater than 0.25 inches.

An alternative to the width and length dimensions above is to design the sensor with an airway sufficient to enable airflow even if the device gets lodged in the throat of the wearer A contributor to choking may be the wearer's ability to separate the sensor device from the exterior surface of the absorbent or auxiliary article being worn (without regard to whether the sensor is designed to be separable). Removal force is the force to separate two layers of a device or article and/or to separate the device from the article. This separation force can be controlled by limiting the ability of the wearer to grasp the device, for example between their finger tips or alternatively by hooking their finger between the device and the article. To minimize the fingertip grasping of the device to promote separation the graspable areas around the sensor may be limited to less than 10 mm or less than 5 mm.

To prevent the wearer from getting their fingers between the sensor and article to separate it the bonds, areas of attachment, between the device and article may desirably have a spacing of no more than 20 mm, less than 15 mm or less than 11 mm. A pocket would help minimize both of these factors especially if the pocket is deeper than the device is long and/or the pocket can be closed (e.g., with hooks and loops). Furthermore if the width of the pocket may desirably be less than 20 mm or less than 15 mm to prevent the wearer from accessing the sensor. In addition, if the sensor is disposed at a depth of at least 5 mm, 10 mm, or 15 mm from the end of the pocket the wearer will likely not be able to reach the sensor for inadvertent removal. In such designs it may be beneficial to provide a means for the caregiver to open the pocket adequately to remove the sensor and/or to provide the caregiver with a means for extracting the sensor from the pocket.

Beyond removal force, it may be desirable to have a shear force between the article and the sensor of from about 10 to about 70 N, 20 to about 60 N, or 30 to about 60 N. The pulling force to separate the sensor from the article may be from about 25 to about 500 N, or 50 to about 250 N.

Thermal Sensor

The sensor of the present disclosure may sense incontinent events by measuring changes associated with the incontinent event. One of the properties of the absorbent article that may be sensed is temperature change of the article associated with introduction of urine or feces associated with an incontinence event. Typical diaper temperatures before urine loading range from about 80 to about 90 degrees Fahrenheit. A urine or fecal insult introduces exudates that are at body temperature, typically 98.6 Fahrenheit, which can be detected through the garment-facing layer of the article. It has been shown that diaper temperature will over time equilibrate into the range of from about 90 to about 92 degrees Fahrenheit after some period of time. Measuring the incontinent event thermally can not only provide an indication of the event itself, but the temperature profile may be used to determine core capacity, and/or size of the insult itself, i.e., amount of urine. The sensor system of the present disclosure may also use the incontinent event as a trigger to review the properties of the wearer and/or the article being monitored before and during the incontinent event. Changes in these properties may show a pattern that can then be used to predict when subsequent incontinent events are likely to occur.

Inductive Sensor

Figure 5A:
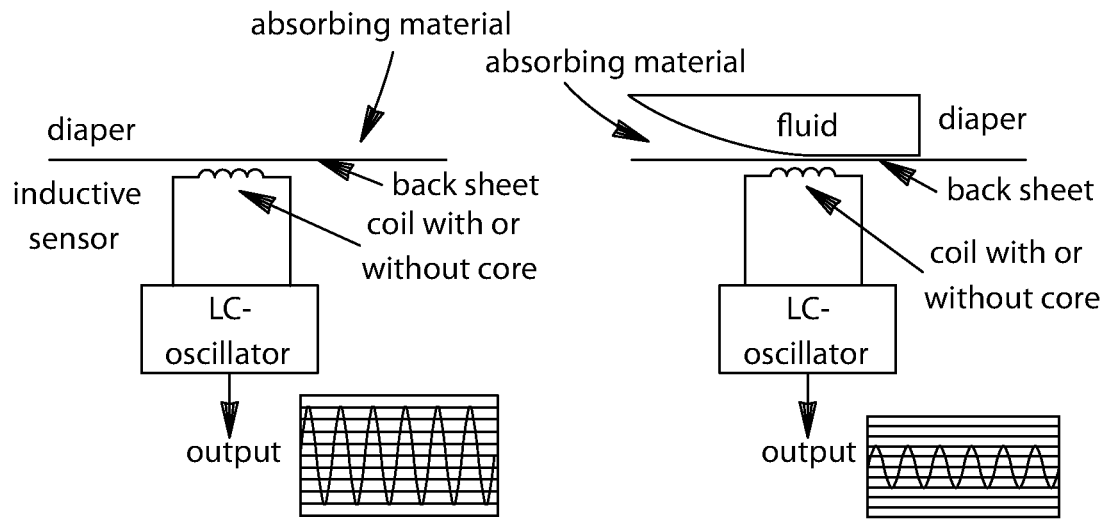
FIGS. 5A-C illustrate an inductive-type sensor, according to embodiments of the present disclosure.
Figure 5B:
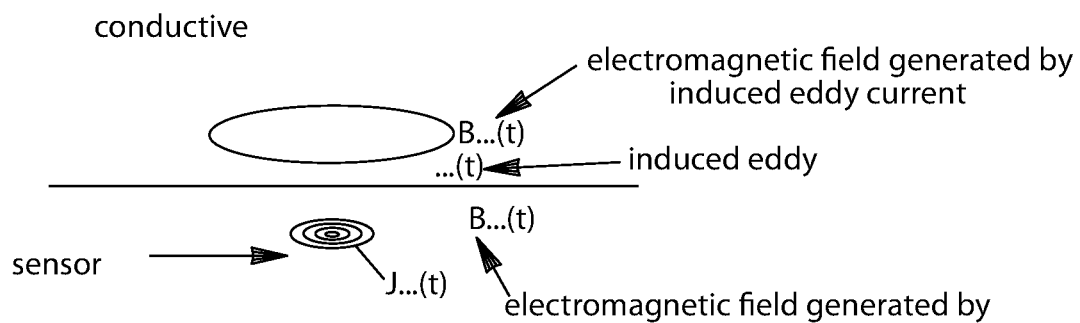
Figure 5C:
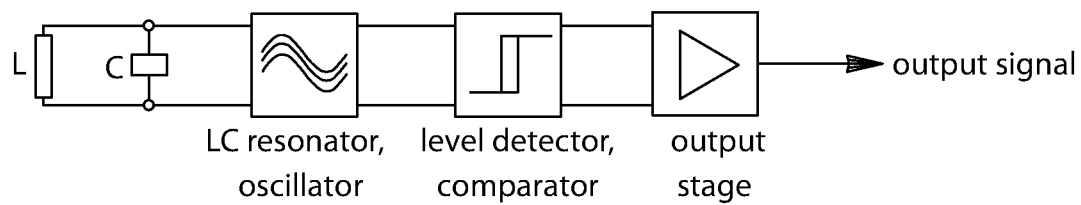
Figure 6A:
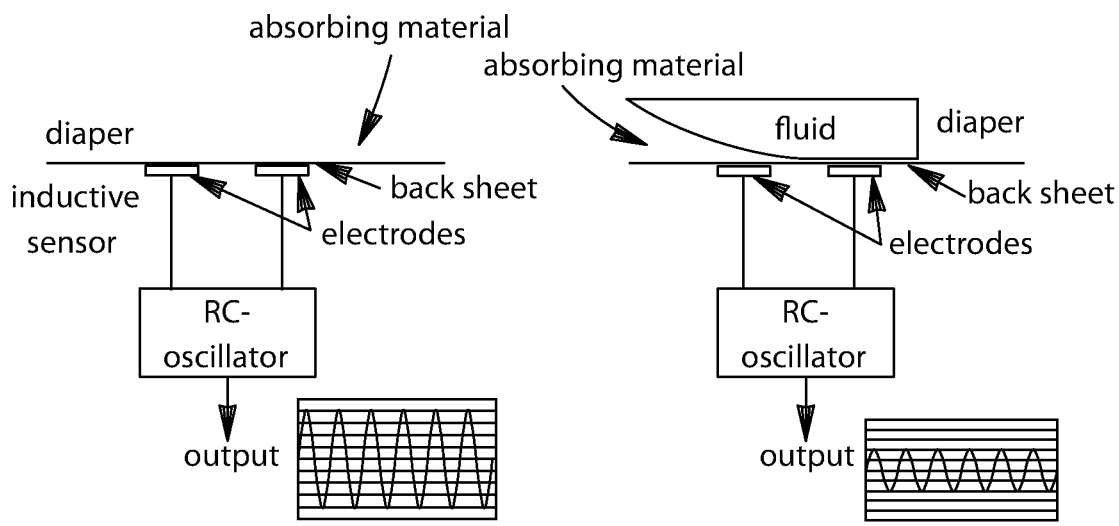
FIGS. 6A-D illustrate a capacitive-type sensor, according to embodiments of the present disclosure.
Figure 6B:
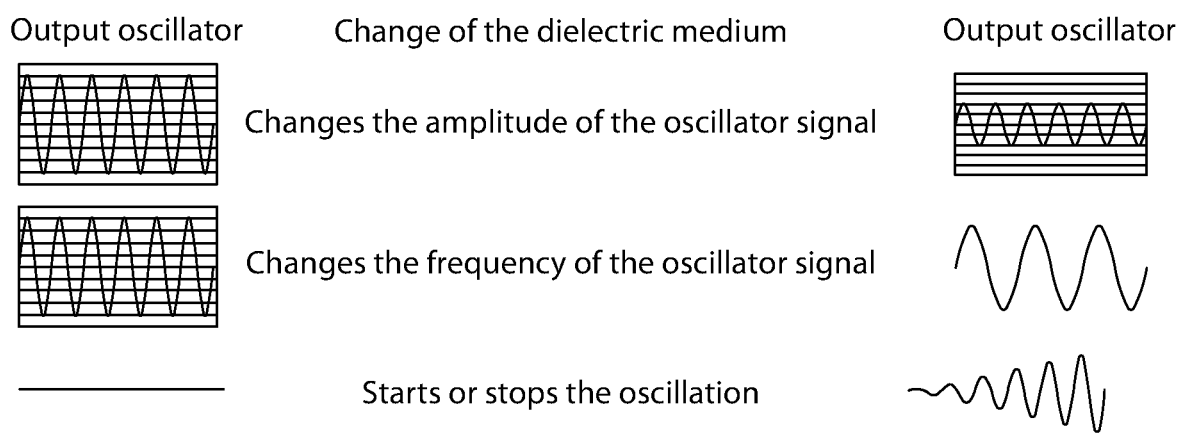
Figure 6C:
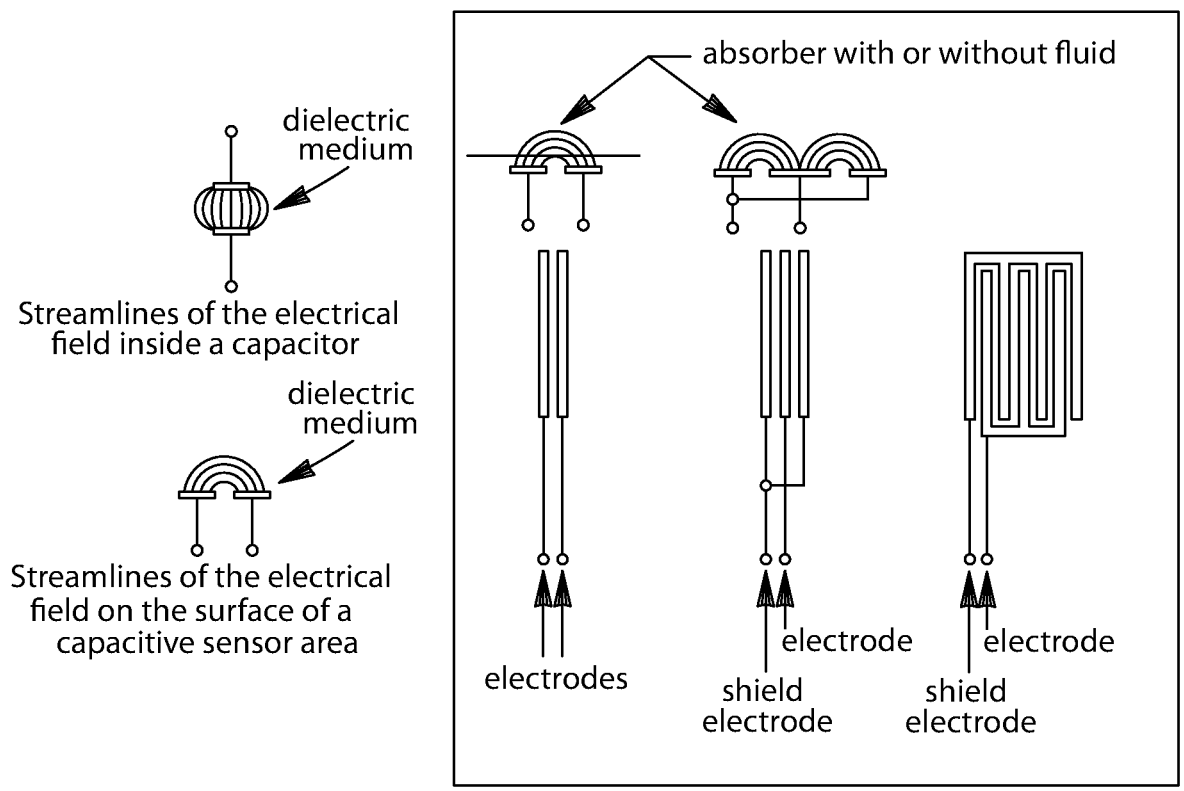
Figure 6D:
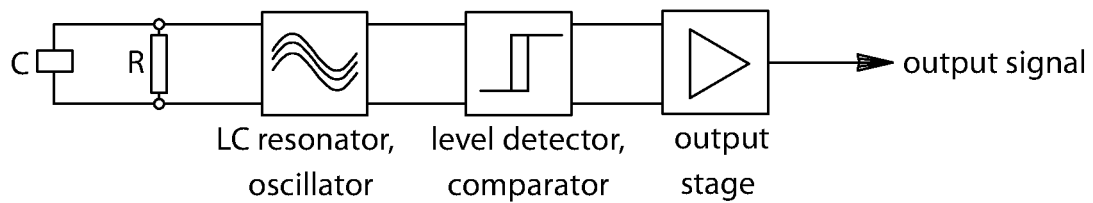

An inductive sensor may be used. Referring generally to FIGS. 5A-C, the inductive sensor may work with a LC-oscillator. This sensor can work by the conductive fluid (urine) damping the oscillating circuit such that the output voltage decreases. Measured data may be gathered from an attached device that detects an change of voltage during urination.

The LC-oscillator may generate a sine wave oscillation at a resonance frequency and an electromagnetic field outside the coil, wherein resonance frequency is $f0=(2\pi*\sqrt{(LC)})-1$. A conductive material within this field will dampen the oscillating circuit by inducing eddy currents inside the material. Conductive material could be metal, carbon, electrically conductive plastics or electrically conductive fluids like saltwater or urine. The damping of the oscillating circuit decreases the output voltage, this change will be detected and evaluation electronics generate an output signal indicative of the change.

Frequency range of the inductive sensor may be from about 10 kHz to about 100 MHz depending on frequency, coil size and distance. Detection distance may be from about 1 to about 20 mm. Coil dimensions may have a diameter from about 5 mm to about 50 mm. Coil geometry may be a solenoid, copper wire coil with or without a core, or may be a flat, pancake coil made of copper wires or may be printed copper coil on PCB (Printed Circuit Board), or as conductive ink or color printed on paper or plastic foil.

Capacitive Sensor

A capacitive sensor may be used. Referring generally to FIGS. 6A-D, a capacitive sensor may work with an RC-oscillator. The sensor works by fluid changing the dielectric and thus increases the capacity of the electrode arrangement. Dependent on the sensor capacity the frequency and the amplitude of the RC-oscillator changes. Measured data may be gathered from an attached device that detects a change of frequency and amplitude during urination.

The capacitive sensor defines the active sensor area. A change of the dielectric medium decreases or increases the capacity of the electrode arrangement and changes the output signal of the oscillation unit.

Capacitive sensors are able to detect solid materials and fluids, independent of the conductivity of the material. The sensitivity and also the detection distance of the capacitive sensor is related to size of the active sensor area and the material and size of the body that should be detected.

Ultra Sonic Sensor

Figure 7B:
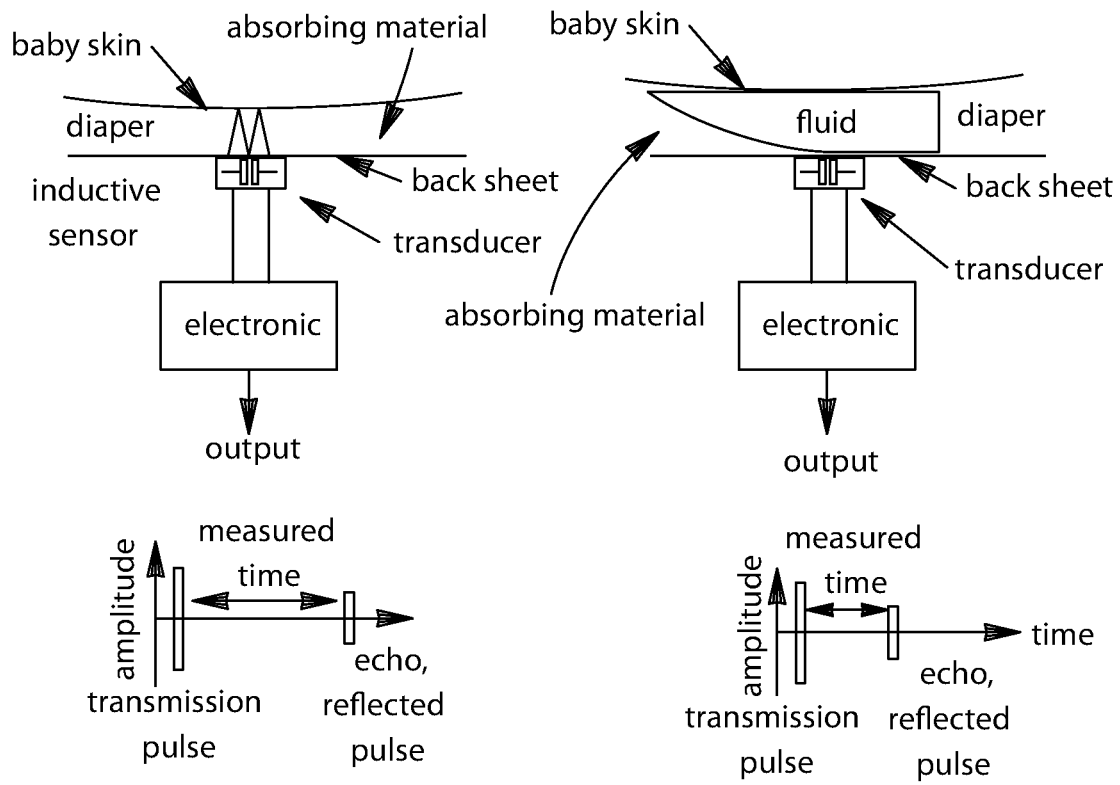
Figure 7B:
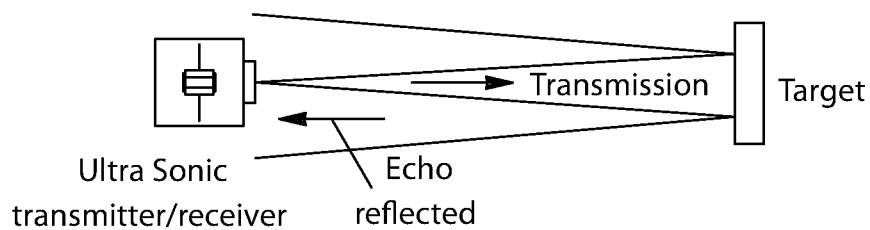
Figure 7B:
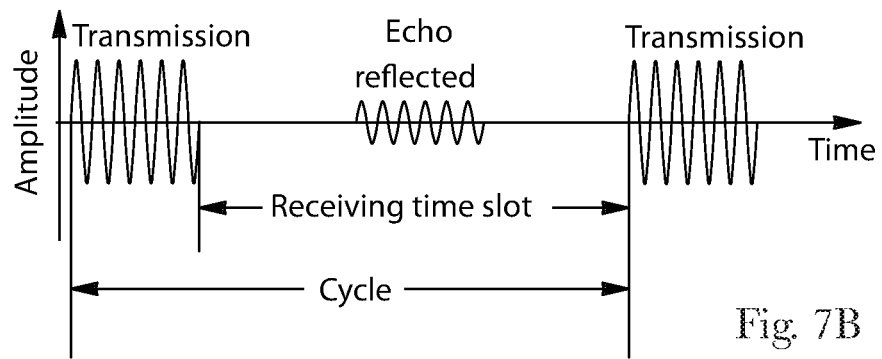
Figure 7C:
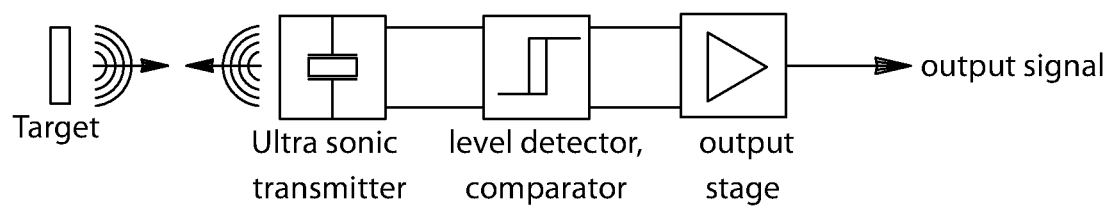

An ultra sonic sensor may be used. Referring generally to FIGS. 7A-C, ultrasonic sensors generate high frequency sound waves in a frequency range from 20 kHz up to 1 GHz.

For distance measurement and object detection they measure the signal run time between transmitted pulse and the echo which is received back by the sensor. Some ultra sonic sensors use separate transmitter and receiver components while others combine both in a single piezoelectric transceiver.

Ultra sonic sensors will work with most of surfaces and also with boundary surfaces between different fluids or gases. The technology is limited by the shapes of surfaces and the density or consistency of the material, but with adapted frequencies and output power is it possible to detect difficult surfaces or materials. Another way to increase the sensor density is to apply variable scan frequencies.

Inside a medium with known density and/or sonic velocity the distance can be calculated as following:

calculation of the distance x based on run time measurement $v = x/t$  $t$=signal run time $x = v^* t$  $x$=distance $v$=inside the medium (in air 346 m/sec)

travel distance of the signal=2 times distance to the object:

$2x = v^* t$ $x = (v^* t)/2$

In case of a single piezoelectric transducer is used the minimum detectable distance is limited by the recovery time of the piezo. The recovery time depends on piezo size, frequency and on electronics.

The measured time difference between transmitted pulse and received pulse is proportional to the distance to the next boundary surface. The emitted power and the transmitter frequency must be configured to penetrate the dry absorbing material and also the garment-facing layer.

Optical Sensor

An alternative sensor approach of the present disclosure senses incontinent events by measuring optical change of the absorbent article associated with a urine or fecal incontinence event. The sensor may simply measure optical changes as urine or feces contact the garment-facing layer of the absorbent article, e.g., change in color associated with the yellow urine or brown feces. Alternatively, the article may comprise a material placed adjacent the garment-facing layer that reacts with the urine of feces insult to change color and provide the optical indication necessary for sensing. In yet another alternative of an optical sensing system the outer cover may comprise a material that changes in translucency when wet, thereby allowing an inner layer to show through creating the optically measurable change. It should be appreciated that these optical changes are desirably reversible after the insult, for example, once the liquid has been absorbed by the absorbent core. Alternatively, it may be desirable that the optical properties change to a measurable degree with each subsequent incontinent event. Measuring the incontinent event optically can not only provide an indication of the event itself, but the duration of the optical change particularly in a reversible change structure can provide an indication of core capacity, product dryness and/or size of the insult itself, e.g. amount of urine. Sensor systems of the present disclosure may also use the incontinent event as a trigger to review the properties of the wearer and/or the article monitored before and during the incontinent event. Changes in these properties may show a pattern that can then be used to predict when subsequent incontinent events are likely.

In an alternative embodiment, a simple absorbent sheet may become darker when liquid is introduced and as liquid is absorbed back into the absorbent core the simple absorbent sheet may become lighter in color. As stated above, it is preferred that the optical changes are either cyclic in nature, i.e., on and off or are progressive in nature, i.e. changing from one level of intensity to another with each loading. These approaches, cyclic and progressive will enable to sensors to distinguish when a loading has occurred and provide reliable indication.

Chemicals and Properties Sensed

In yet another alternative embodiment, sensors of the present disclosure monitor incontinent events by measuring changes associated with an incontinent event. One of the properties of the absorbent article that may be monitored is transmission of a specific gas or vapor through the article outer cover. The creation of the gas or vapor may be associated with a urine and/or fecal incontinence event. Microporous, breathable outer covers have the ability to pass gases and/or vapors through the pores of the outer cover itself. The monitoring involves one or more reactants that create or generate a gas or vapor when contacted by urine and/or feces. It should be appreciated that the selective gas and/or vapor transmission through the outer cover is desirably cyclic, i.e., lower once the liquid has been absorbed and high when free liquid is present. The magnitude of the cyclic nature of the reactant needs only be sufficient for reliable sensing of the event. Measuring the incontinent event via moisture vapor transmission can not only provide an indication of the event itself, but the moisture vapor transmission profile or threshold values may be used to determine core capacity, product dryness and/or size of the insult itself, e.g., amount of urine. Further, the incontinent event may act as a trigger to review the properties of the wearer and/or the article being monitored before and during the incontinent event. Changes in these properties may show patterns which can then be used to predict when subsequent incontinent events are likely.

Communication

There are a number of acceptable orientations for placing sensors in or on the auxiliary article to ensure the desired sensing of the environment within the absorbent article. For instance, an aperture or absorbent free zone may be created in the core of the absorbent article so that fecal waste or urine are more readily disposed against the garment-facing layer and thereby provide a strong enough stimulus (e.g., chemical, visual, etc.) that is detectable by the sensor. For this purpose, use of a substantially air felt free core may be desirable. Examples of acceptable air felt free cores are disclosed in U.S. Pat. Nos. 5,562,646, 7,750,203, 7,744,576 and U.S. Pub. Nos. 2008/0312617A1, 2008/0312619A1, 2004/0097895A1.

Alternatively, the sensor may comprise a mechanical fastener, e.g., a hook-like material that can engage with the outer surface of the product, nonwoven or loop material to hold the sensor in place. In an alternative approach the sensor may comprise a magnet designed to pull the sensor into contact with the external surface of the absorbent article. In such a design the article may comprise a thin piece of magnetically compatible material.

Sensors of the present disclosure may be designed to predict when an incontinent event may happen. For example, in one embodiment, the sensor may monitor a property of an absorbent article while the article is being worn. The sensor may determine a change in the property of the absorbent article wherein the change is indicative of an incontinent event of the wearer. Further, the sensor may predict conditions indicative of a subsequent incontinent event based on the change in a property. The sensor may make predictions by comparing a series of incontinent events and conditions present at, during or before the incontinent events, and by determining patterns in the conditions present at, during or before the incontinent events. Further, the sensor may provide an insult notification to inform a caregiver and/or the wearer of the presence of an insult in the absorbent article.

Moisture Vapor Transmission

In yet another alternative embodiment, the sensors of the present disclosure may sense incontinent events by measuring changes in moisture vapor transmission through the absorbent article garment-facing layer. Microporous, breathable garment-facing layers have the ability to pass moisture vapor through the pores of the layer itself. The rate of transmission is highly dependent on the distance the liquid is from the surface of the microporous material. Typical microporous materials exhibit significantly higher "wet cup" moisture vapor transmission rates (liquid directly on the surface of the material) than "dry cup" moisture vapor transmission rates (high humidity on one side low humidity on the other). Therefore, such microporous materials will have a higher moisture vapor transmission rate during and immediately after the incontinence event, especially for urine and watery feces, than during the remainder of the wearing time, when the diaper is dry or once the absorbent materials have contained all of the free liquid. It may be desirable to use a breathable garment-facing layer for the purpose of measuring WVTR. WVTRs of garment-facing layers of the present disclosure may range from about 500 to about 8,000, from about 1,000 to about 6,000, or from about 2,000 to about 4,000 $g/m^2/24$ hours (as determined by ASTM E96).

The sensor system of the present disclosure may monitor a second property which is indicative of an intake of a substance by the wearer such a liquid, a solid, or a drug. For example this property may be data the wearer or caregiver may enter via a wireless handheld device or computer comprising a keyboard, mouse or touchpad indicating that the wearer has consumed food and/or liquids or has been given a drug. A pattern may show that at a given time after eating and/or drinking an incontinent event may occur.

The sensor system may predict conditions indicative of a subsequent incontinent event a number of ways. The sensor system may compare the changes in the first and the second properties that are being monitored and compare them with known patterns predictive of incontinent events. Alternatively the sensor system may look for individual incontinent events as indicated by the first property and then looked to changes in the second property which preceded the incontinent event. Upon finding an instance of a change in the second property followed by an incontinent event, the sensor system may then compare other incontinent events for a similar cause and effect relationship. Multiple second properties may be compared to find more complex relationships and patterns.

Sustainability

There is a growing desire to utilize more sustainable absorbent articles. It is too costly and too wasteful to incorporate a sensor into each article, and to throw it away with each absorbent article change. Instead of throwing away hundreds or thousands of disposable sensors per wearer, a single external sensor in an auxiliary article may be reused. The sensor may be oriented in a washable, reusable auxiliary article.

Another advantage of using a single sensor outside the absorbent article is that the sensor may be used with any absorbent article, including brand, type (taped, pull-on diapers, training pants, etc.), size (e.g., infant to adult).

Internal sensors and/or sensors that are part of the absorbent article may require a built in power source that needs to last through the storage and shelf-life of the absorbent article it is incorporated into. Sensors that are removable from the absorbent article and/or auxiliary article may be set in a recharging base or may have replaceable batteries. Alternatively, especially for auxiliary articles, a battery that is integral with the article may be recharged via a port in the article capable of receiving a charging wire that may be plugged into an outlet.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A system for detecting a property associated with a disposable absorbent article, the system comprising:
   a. a reusable sensor device comprising sensors for detecting temperature, humidity, and vapor compounds of feces; and
   b. an auxiliary article comprising a garment including a pocket, recess or void for receiving the sensor device via the pocket, recess, or void defined in the auxiliary article garment, wherein the sensor device is removable from the auxiliary article garment;
   c. a monitoring function indicative of an intake of a liquid, a solid, or a drug via manual data entry by a caregiver;
   d. wherein the auxiliary article garment is configured for temporary attachment to and removal from the disposable absorbent article.

2. The system of claim 1, wherein the disposable absorbent article comprises a garment-facing layer comprising a film and a nonwoven layer.

3. The system of claim 2, wherein the garment-facing layer has a water vapor transmission rate value of from 500-8,000 g/m$^2$/24 hours according to ASTM E96.

4. The system of claim 1, wherein the reusable sensor device further comprises a battery.

5. The system of claim 1, wherein the auxiliary article garment is configured to fit over the disposable absorbent article.

6. The system of claim 5, wherein the auxiliary article garment comprises a pant-type auxiliary article having preformed waist and leg openings.

7. The system of claim 5, wherein the auxiliary article garment comprises one of a front-fastenable auxiliary article, a rear-fastenable auxiliary article or side-fastenable auxiliary article.

8. A system for detecting a property associated with a disposable absorbent article, the system comprising:
   a. a reusable sensor device comprising sensors for detecting temperature, humidity, and vapor compounds of feces; and
   b. an auxiliary article comprising a garment including a pocket, recess or void for receiving the sensor device via the pocket, recess, or void defined in the auxiliary article garment, wherein the sensor device is removable from the auxiliary article garment;
   c. wherein the auxiliary article garment is configured for temporary attachment to and removal from the disposable absorbent article; and
   d. wherein the auxiliary article garment comprises a window disposed within a layer thereof to provide communication between the sensor device and the disposable absorbent article.

9. The system of claim 8, wherein the disposable absorbent article comprises a garment-facing layer comprising a film and a nonwoven layer, and wherein the film is vapor permeable.

10. The system of claim 9, wherein the garment-facing layer has a water vapor transmission rate value of from 500-8,000 g/m$^2$/24 hours according to ASTM E96.

11. The system of claim 8, further comprising a monitoring function indicative of an intake of a liquid, a solid, or a drug via manual data entry by a caregiver.

12. The system of claim 8, wherein the reusable sensor device further comprises a battery.

13. The system of claim 8, wherein the auxiliary article garment is configured to fit over the disposable absorbent article.

14. The system of claim 13, wherein the auxiliary article garment comprises a pant-type auxiliary article having preformed waist and leg openings.

15. The system of claim 13, wherein the auxiliary article garment comprises one of a front-fastenable auxiliary article, a rear-fastenable auxiliary article or side-fastenable auxiliary article.

16. A system for detecting a property associated with a disposable absorbent article, the system comprising:
   a. a reusable sensor device comprising sensors for detecting temperature and vapor compounds; and
   b. an auxiliary article comprising a garment including a pocket, recess or void for receiving the sensor device via the pocket, recess, or void defined in the auxiliary article garment, wherein the sensor device is removable from the auxiliary article garment;
   c. wherein the auxiliary article garment is configured for temporary attachment to and removal from the disposable absorbent article; and
   d. wherein the auxiliary article garment comprises a window disposed within a layer thereof to provide communication between the sensor device and the disposable absorbent article.

17. The system of claim 16, wherein the disposable absorbent article comprises a garment-facing layer comprising a film and a nonwoven layer, and wherein the film is vapor permeable.

18. The system of claim 17, wherein the garment-facing layer has a water vapor transmission rate value of from 500-8,000 g/m$^2$/24 hours according to ASTM E96.

19. The system of claim 16, further comprising a monitoring function indicative of an intake of a liquid, a solid, or a drug via manual data entry by a caregiver.

20. The system of claim 16, wherein the reusable sensor device further comprises a battery.

* * * * *